United States Patent
Gross et al.

(10) Patent No.: US 8,095,218 B2
(45) Date of Patent: Jan. 10, 2012

(54) GI AND PANCREATIC DEVICE FOR TREATING OBESITY AND DIABETES

(75) Inventors: Yossi Gross, Moshav Mazor (IL); Jacob Benarie, Haifa (IL); Radwan Khawaled, Shfar-Am (IL); Ruth Alon, Michmoret (IL)

(73) Assignee: Betastim, Ltd., Caesarea (IL)

( * ) Notice: Subject to any disclaimer, the term of this patent is extended or adjusted under 35 U.S.C. 154(b) by 852 days.

(21) Appl. No.: 11/995,663

(22) PCT Filed: Jul. 13, 2006

(86) PCT No.: PCT/IL2006/000819
§ 371 (c)(1),
(2), (4) Date: Apr. 10, 2008

(87) PCT Pub. No.: WO2007/007339
PCT Pub. Date: Jan. 18, 2007

(65) Prior Publication Data
US 2009/0062881 A1 Mar. 5, 2009

Related U.S. Application Data

(63) Continuation-in-part of application No. 11/279,355, filed on Apr. 11, 2006.

(60) Provisional application No. 60/699,442, filed on Jul. 13, 2005, provisional application No. 60/720,951, filed on Sep. 26, 2005.

(51) Int. Cl.
*A61N 1/36* (2006.01)

(52) U.S. Cl. .............................. 607/40; 607/41; 607/133

(58) Field of Classification Search ................... 607/40, 607/41, 133
See application file for complete search history.

(56) References Cited

U.S. PATENT DOCUMENTS

| | | |
|---|---|---|
| 4,416,267 A | 11/1983 | Garren et al. |
| 4,694,827 A | 9/1987 | Weiner et al. |
| 4,723,547 A | 2/1988 | Kullas et al. |
| 4,739,758 A | 4/1988 | Lai et al. |
| 4,899,747 A | 2/1990 | Garren et al. |
| 5,188,104 A | 2/1993 | Wernicke |
| 5,234,454 A | 8/1993 | Bangs |
| 5,263,480 A | 11/1993 | Wernicke et al. |
| 5,423,872 A | 6/1995 | Cigaina |
| 5,541,951 A | 7/1996 | Juhasz et al. |
| 5,690,691 A | 11/1997 | Chen et al. |

(Continued)

FOREIGN PATENT DOCUMENTS

EP 1392393 3/2004
(Continued)

OTHER PUBLICATIONS

PCT International Preliminary Report on Patentability for PCT International Application No. PCT/IL2006/000819 issued Mar. 31, 2009.
(Continued)

*Primary Examiner* — Scott Getzow
*Assistant Examiner* — Joseph Dietrich
(74) *Attorney, Agent, or Firm* — RatnerPrestia

(57) ABSTRACT

A method is provided, including placing first and second electrodes (90) at respective first and second sites of a duodenum (40) of a subject, and activating the electrodes (90) to increase a blood insulin level of the subject. Other embodiments are also described.

45 Claims, 12 Drawing Sheets

U.S. PATENT DOCUMENTS

| | | |
|---|---|---|
| 5,868,141 A | 2/1999 | Ellias |
| 5,919,216 A | 7/1999 | Houben et al. |
| 5,987,060 A | 11/1999 | Grenon et al. |
| 6,091,992 A | 7/2000 | Bourgeois et al. |
| 6,135,978 A | 10/2000 | Houben et al. |
| 6,191,102 B1 | 2/2001 | DiMarchi et al. |
| 6,215,287 B1 | 4/2001 | Matsushiro et al. |
| 6,322,560 B1 | 11/2001 | Garbagnati et al. |
| 6,454,785 B2 | 9/2002 | De Hoyos Garza et al. |
| 6,571,127 B1 | 5/2003 | Ben-Haim et al. |
| 6,575,969 B1 | 6/2003 | Rittman, III et al. |
| 6,579,301 B1 | 6/2003 | Bales et al. |
| 6,684,105 B2 | 1/2004 | Cohen et al. |
| 6,733,512 B2 | 5/2004 | McGhan |
| 6,826,428 B1 | 11/2004 | Chen et al. |
| 6,832,114 B1 | 12/2004 | Whitehurst et al. |
| 6,836,515 B1 | 12/2004 | Kay et al. |
| 6,853,862 B1 | 2/2005 | Marchal et al. |
| 6,895,279 B2 | 5/2005 | Loeb et al. |
| 6,993,391 B2 | 1/2006 | Flesler et al. |
| 7,006,871 B1 | 2/2006 | Darvish et al. |
| 7,016,296 B2 | 3/2006 | Hartman, Jr. |
| 7,047,029 B1 | 5/2006 | Godwin et al. |
| 2002/0072779 A1 | 6/2002 | Loeb |
| 2003/0055464 A1 | 3/2003 | Darvish et al. |
| 2003/0055467 A1 | 3/2003 | Ben-Haim et al. |
| 2003/0158569 A1 | 8/2003 | Wazne |
| 2003/0181958 A1 | 9/2003 | Dobak, III |
| 2004/0088022 A1* | 5/2004 | Chen .............................. 607/40 |
| 2004/0172084 A1 | 9/2004 | Knudson et al. |
| 2004/0172085 A1 | 9/2004 | Knudson et al. |
| 2004/0172088 A1 | 9/2004 | Knudson et al. |
| 2004/0176685 A1 | 9/2004 | Takizawa et al. |
| 2004/0176812 A1 | 9/2004 | Knudson et al. |
| 2004/0249421 A1 | 12/2004 | Harel et al. |
| 2005/0004430 A1 | 1/2005 | Lee et al. |
| 2005/0007232 A1 | 1/2005 | Ono et al. |
| 2005/0021101 A1 | 1/2005 | Chen et al. |
| 2005/0075078 A1 | 4/2005 | Makinen et al. |
| 2005/0085923 A1 | 4/2005 | Levine et al. |
| 2005/0137633 A1 | 6/2005 | Salo et al. |
| 2006/0085045 A1 | 4/2006 | Harel et al. |
| 2007/0016262 A1 | 1/2007 | Gross et al. |

FOREIGN PATENT DOCUMENTS

| | | |
|---|---|---|
| WO | WO-87/00034 | 1/1987 |
| WO | WO 87/00034 | 1/1987 |
| WO | WO-99003533 | 1/1999 |
| WO | WO 00/53257 | 9/2000 |
| WO | WO-00/53257 | 9/2000 |
| WO | WO-0053257 | 9/2000 |
| WO | WO-00/76114 | 12/2000 |
| WO | WO-02/092165 | 11/2002 |
| WO | WO 02/092165 A1 | 11/2002 |
| WO | WO-03/018118 | 3/2003 |
| WO | WO 03/018118 A1 | 3/2003 |
| WO | WO-03/045493 | 6/2003 |
| WO | WO 03/045493 A2 | 6/2003 |
| WO | WO-03/055420 | 7/2003 |
| WO | WO 03/055420 A1 | 7/2003 |
| WO | WO-2004/021858 | 3/2004 |
| WO | WO 2004/021858 A2 | 3/2004 |
| WO | WO-2004/089262 | 10/2004 |
| WO | WO 2004/089262 A2 | 10/2004 |
| WO | WO 2004/112563 A2 | 12/2004 |
| WO | WO-2004112563 | 12/2004 |
| WO | WO-2005/007232 | 1/2005 |
| WO | WO 2005/007232 A2 | 1/2005 |
| WO | WO-2005/023081 | 3/2005 |
| WO | WO 2005/023081 A2 | 3/2005 |
| WO | WO-2005/051486 | 6/2005 |
| WO | WO 2005/051486 A1 | 6/2005 |
| WO | WO-2005/087310 | 9/2005 |
| WO | WO 2005/087310 A2 | 9/2005 |
| WO | WO-2006/018851 | 2/2006 |
| WO | WO 2006/018851 B2 | 2/2006 |

OTHER PUBLICATIONS

Gershon, "The Enteric Nervous System: A Second Brain", Hospital Practice, Jul. 15, 1999, 31-42.

Todd et al., "Glucagon-like peptide-1 (GLP-1): a trial of treatment in non-insulin-dependent diabetes mellitus", European Journal of Clinical Investigation (1997) 27, 533-536.

Gutniak et al., "Subcutaneous Injection of the Incretin Hormone Glucagon-Like Peptide 1 Abolishes Postprandial Glycemia in NIDDM", Diabetes Care, vol. 17, No. 9, Sep. 1994, 1039-1044.

Robertson et al., "The influence of the colon on postprandial glucagon-like peptide 1 (7-36) amide concentration in Man" Journal of Endocrinology (1999) 161, 25-31.

Schirra et al., "Mechanisms of the antidiabetic action of subcutaneous glucagon-like peptide-1 (7-36) amide in non-insulin dependent diabetes mellitus", Journal of Endocrinology (1998) 156, 177-186.

Todd et al., "Subcutaneous glucagon-like peptide-1 improves postprandial glycaemic control over a 3-week period in patients with early Type 2 diabetes", Clinical Science (1998) 95, 325-329.

Vilsboll et al., "Reduced Postprandial Concentrations of Intact Biologically Active Glucagon-Like Peptide 1 in Type 2 Diabetic Patients", Diabetes, vol. 50, Mar. 2001, 609-613.

Kalloo et al., "Flexible transgastric peritoneoscopy: a novel approach to diagnostic and therapeutic interventions in the peritoneal cavity", Gastrointestinal Endoscopy, vol. 60, No. 1, 2004, 114-117.

Sun et al., "Intestinal Electric Stimulation Decreases Fat Absorption in Rats: Therapeutic Potential for Obesity", Obesity Research, vol. 12, No. 8, Aug. 2004, 1235-1242.

Giralt et al., "Inhibition by CCK of ascending contraction elicited by mucosal stimulation in the duodenum of the rat", Neurogastroenterol. Mot (2000) 12, 173-180.

Mukhopadhyay et al., "Effect of cholecystokinin on myoelectric activity of small bowel of the dog", Am. J. Physiol. 232(1): E44-E47, 1977.

Bergman et al., "The evolution of β-cell dysfunction and insulin resistance in type 2 diabetes", European Journal of Clinical Investigation (2002) 32 (Suppl. 3), 35-45.

Chiasson et al., "Prevention of Type 2 Diabetes Insulin Resistance and β-Cell Function", Diabetes, vol. 53, Supplement 3, Dec. 2004, S34-S38.

Kahn, "The relative contributions of insulin resistance and beta-cell dysfunction to the pathophysiology of Type 2 diabetes", Diabetologia (2003) 46:3-19.

Toyama et al., "Effect of Ethanol on Pancreatic Interstitial pH and Blood Flow in Cats with Chronic Pancreatitis", Annals of Surgery, vol. 225, No. 2, 223-228.

Liu et al., "Therapeutic Potential of Duodenal Electrical Stimulation for Obesity: Acute Effects on Gastric Emptying and Water Intake", American Journal of Gastroenterology, 2005, 100:792-796.

Zhao et al., "Electric stimulation of small intestine delays gastric emptying in the dog model", (abstract) Neurogastroenterol Motil 14:457 (2002).

Qian et al., "Normalization of atropine-induced postprandial dysrhythmias with gastric pacing", Am J Physiol. 276 (Gastrointest. Liver Physiol. 39): G387-G392, 1999.

Chen et al., "Gastric Electrical Stimulation With Short Pulses Reduces Vomiting but not Dysrhythmias in Dogs", Gastroenterology 2003:124:401-409.

Rocca et al., "Role of the Vagus Nerve in Mediating Proximal Nutrient-Induced Glucagon-Like Peptide-1 Secretion", Endocrinology (1999), vol. 140, No. 4, 1687-1694.

U.S. Appl. No. 60/699,442, filed Jul. 13, 2005.

U.S. Appl. No. 60/720,951, filed Sep. 26, 2005.

Supplementary European Search Report dated Sep. 11, 2009, which issued during the prosecution of Applicants' European Patent Application No. EP 06 76 6139.

An Office Action dated Aug. 19, 2009, which issued during the prosecution of Applicants' U.S. Appl. No. 11/279,355.

An Office Action dated Aug. 19, 2009, which issued during the prosecution of Applicants' U.S. Appl. No. 11/965,997.

* cited by examiner

GI AND PANCREATIC DEVICE FOR TREATING OBESITY AND DIABETES

CROSS-REFERENCES TO RELATED APPLICATIONS

The present patent application is a continuation-in-part of U.S. application Ser. No. 11/279,355, filed Apr. 11, 2006, entitled, "GI and pancreatic device for treating obesity and diabetes," which is currently pending, which published as US 2007/0016262 to Gross, and which claims the benefit of:
(a) U.S. Provisional Patent Application 60/699,442 to Alon and Gross, filed Jul. 13, 2005, entitled, "GI and pancreatic device for treating obesity and diabetes," and
(b) U.S. Provisional Patent Application 60/720,951 to Alon and Gross, filed Sep. 26, 2005, entitled, "GI and pancreatic device for treating obesity and diabetes."

Each of these applications is incorporated herein by reference.

FIELD OF THE INVENTION

The present invention relates generally to treating obesity and diabetes, and specifically to methods and apparatus that treat obesity and diabetes from within the gastrointestinal tract and pancreas.

BACKGROUND OF THE INVENTION

Obesity and diabetes are frequently linked diseases, although some patients with one condition do not suffer from the other. The multiple causes of obesity are a subject of ongoing research. Insulin resistance and beta-cell dysfunction are two important factors contributing to the development of diabetes. The relationship between these two factors has been extensively studied, as has the role of obesity in diabetes. In particular, it has been widely observed that obesity is a principal cause of insulin resistance. Most patients who develop type II diabetes are obese.

As described in an article by Michael Gershon entitled, "The enteric nervous system: A second brain" (Hospital Practice, July, 1999), which is incorporated herein by reference, the enteric nervous system (ENS) is a portion of the autonomic nervous system which consists of two layers. The first layer is called the myenteric (Auerbach's) plexus, and lies between the layers of circular and longitudinal muscle lining the gut wall. The second layer is called the submucosal plexus, and lies between the layer of circular muscle and the submucosa. The myenteric plexus contains neurons responsible for motility and for mediating the enzyme output of adjacent organs. The smaller, submucosal (Meissner's) plexus contains sensory cells that communicate with the neurons of the myenteric plexus, as well as motor fibers that stimulate secretion from epithelial crypt cells into the gut lumen. Electrical coupling between smooth muscle cells enables signals to rapidly alter the membrane potential of even those cells that have no direct contact with neurons and ensures that large regions of bowel—rather than small groups of muscle cells—will respond to nerve stimulation.

PCT Patent Publication WO 2005/007232 to Ben-Haim et al., which is incorporated herein by reference, describes a method and apparatus for treating a subject. An electrical signal is applied to at least one stomach site of the subject. The electrical signal is configured to reduce a rise in a blood glucose level of the subject, in order to treat the subject. A colonic stimulation system is also described, comprising a control unit and one or more electrodes, which are adapted to be applied to respective sites in a vicinity of a colon or a distal small intestine of a patient. The control unit drives the electrodes to apply electrical signals to the sites, and configures the signals to stimulate L-cells or other target tissue, which, responsive to such stimulation, increase secretion of glucagon-like-peptide-1 (GLP-1). Such secretion of GLP-1 is described as generally improving glycemic control of the patient, and therefore serving to treat patients suffering from insulin-resistance-related conditions, such as obesity, NIDDM, heart disease, and hypertension, or healthy patients considered at risk for such conditions. For some applications, the colonic stimulation system further comprises an eating detection unit, and the control unit is configured to drive the electrodes to apply the signals responsive to a detection of eating.

U.S. Pat. No. 6,091,992 to Bourgeois et al., which is incorporated herein by reference, describes a method and apparatus for providing electrical stimulation to the gastrointestinal tract. The apparatus features an implantable pulse generator which may be coupled to the gastric system through one or more medical electrical leads. In the preferred embodiment the leads couple to the circular layer of the stomach. In one embodiment, the implantable system includes a hermetically sealed implantable pulse generator, the pulse generator emitting a first type of electrical stimulation at a first rate and a second type of electrical stimulation at a second rate.

The following patent publication and articles, all of which are incorporated herein by reference, may be of interest:
U.S. Pat. No. 6,191,102 to DiMarchi et al.
Todd J F et al., "Glucagon-like peptide-1 (GLP-1): a trial of treatment in non-insulin-dependent diabetes mellitus," Eur J Clin Invest 27(6):533-6 (1997)
Gutniak M K et al., "Subcutaneous injection of the incretin hormone glucagon-like peptide 1 abolishes postprandial glycemia in NIDDM," Diabetes Care 17(9):1039-44 (1994)
Robertson M D et al., "The influence of the colon on postprandial glucagon-like peptide 1 (7-36) amide concentration in man," J Endocrinol 161(1):25-31 (1999)
Schirra J et al., "Mechanisms of the antidiabetic action of subcutaneous glucagon-like peptide-1 (7-36) amide in non-insulin dependent diabetes mellitus," J Endocrinol 156(1):177-86 (1998)
Todd J F et al., "Subcutaneous glucagon-like peptide-1 improves postprandial glycaemic control over a 3-week period in patients with early type 2 diabetes," Clin Sci (Lond) 95(3):325-9 (1998)
Vilsboll T et al., "Reduced postprandial concentrations of intact biologically active glucagon-like peptide 1 in type 2 diabetic patients," Diabetes 50(3):609-13 (2001)
Zhao X T et al., "Electric stimulation of small intestine delays gastric emptying in the dog model" [abstract], Neurogastroenterol Motil 14: 457 (2002)
Qian L W et al., "Normalization of atropine-induced postprandial dysrhythmias with gastric pacing," Am J Physiol 276:G387-92 (1999)
Chen J D Z et al., "Gastric electrical stimulation with short pulses reduces vomiting but not dysrhythmias in dogs," Gastroenterology 124: 401-9 (2003).

U.S. Pat. No. 6,322,560 to Garbagnati et al., which is incorporated herein by reference, describes a catheter for the treatment of tumors by hyperthermia induced by radiofrequency or other energy. The catheter comprises a tubular body having a cooled metal plate capable of acting as an active electrode. One application described is the treatment of pancreatic tumors by introducing the catheter through the main pancreatic duct by endoscopy or during surgery.

U.S. Pat. No. 6,575,969 to Rittman, III et al., which is incorporated herein by reference, describes a fluid-cooled (perfusion-cooled) high-frequency electrode. In one embodiment, the electrode comprises a "stint," a balloon, or a condom-like structure that can be inserted into the pancreatic duct, and by appropriate cooling in conjunction with RF heating, it can "throw" the heat into a pancreatic tumor while sparing the structure of the duct to preserve normal processing of biological fluids.

U.S. Pat. No. 5,188,104 to Wernicke et al., which is incorporated herein by reference, describes a method for treating patients with compulsive eating disorders, including detecting a preselected event indicative of an imminent need for treatment of the specific eating disorder of interest, and responding to the detected occurrence of the preselected event by applying a predetermined stimulating signal to the patient's vagus nerve appropriate to alleviate the effect of the eating disorder of interest. For example, the preselected event may be a specified level of food consumption by the patient within a set interval of time, or the commencement of a customary mealtime according to the patient's circadian cycle, or the passage of each of a sequence of preset intervals of time, or the patient's own recognition of the need for treatment by voluntarily initiating the application of the stimulating signal to the vagus nerve. In cases in which the disorder is compulsive eating to excess, the stimulating signal is described as being predetermined to produce a sensation of satiety in the patient.

US Patent Application Publication 2005/0021101 to Chen et al., which is incorporated herein by reference, describes a method for regulating gastrointestinal action in a subject using a stimulatory electrode and a sensor to provide retrograde feedback control of electrical stimulation to the GI tract. Also described is a method for reducing weight in a subject, using a stimulatory electrode and a sensor to provide retrograde feedback control of electrical stimulation to the stomach. Further described is a method for providing electrical field stimulation to a gastrointestinal organ, as well as a method of providing an electrical potential gradient in a gastrointestinal organ. Further described is a method for stimulating the vagus nerve of a subject, by positioning a stimulatory electrode in a gastrointestinal organ of the subject. Additionally described is a method of placing a device in the gastrointestinal tract or wall of a subject from the exterior of the subject, using a needle to insert the device.

PCT Publication WO 00/53257 to Darwish et al., which is incorporated herein by reference, describes a pancreatic controller comprising a glucose sensor; at least one electrode, for electrifying an insulin producing cell or group of cells; a power source for electrifying the electrode with a pulse that does not initiate an action potential in the cell and has an effect of increasing insulin secretion; and a controller which receives the sensed level and controls the power source to electrify the electrode to have a desired effect on the level.

US Patent Application Publication 2003/0055464 to Darvish et al., which is incorporated herein by reference, describes a pancreatic controller comprising at least one electrode adapted for electrifying at least a portion of a pancreas; and a controller programmed to electrify the electrode so as to positively control at least the effect of at least two members of a group consisting of blood glucose level, blood insulin level and blood level of another pancreatic hormone.

PCT Publications WO 04/021858 and WO 05/023081 to Harel et al., which are incorporated herein by reference, describe a method for glucose level control, comprising providing at least one electrode adapted to apply an electric field to a pancreas, and applying an electric field to the pancreas using the electrode such that blood glucose levels are significantly reduced and blood insulin levels are not significantly increased.

PCT Publication WO 03/045493 to Harel et al., which is incorporated herein by reference, describes apparatus for sensing electrical activity of the pancreas. The apparatus includes a set of one or more electrodes, adapted to be coupled to the pancreas, and to generate activity signals indicative of electrical activity of pancreatic cells which are in a plurality of islets of the pancreas.

US Patent Application Publication 2004/0249421 to Harel et al., which is incorporated herein by reference, describes a method for glucose level control, comprising applying an electric field to the pancreas using at least one electrode such that blood glucose levels are significantly reduced, and blood insulin levels are not significantly increased compared to a regular insulin response in a same person. Also described are methods for implanting the electrodes in the pancreas, including: (a) advancing an endoscope to a bile duct, for example via the stomach, and advancing the endoscope through the bile ducts along the pancreas; and (b) advancing an endoscope to the duodenum or other portion of the intestine adjacent to the pancreas, and extending electrodes from the intestine into the pancreas.

U.S. Pat. No. 6,853,862 to Marchal et al., which is incorporated herein by reference, describes a gastroelectric stimulator comprising a neurostimulator for producing a stimulation signal, at least one electrical lead, and at least two electrical contacts. The stimulation signal is adapted to influence pancreatic secretions.

U.S. Pat. No. 5,919,216 to Houben et al., which is incorporated herein by reference, describes a system for automatically responding to insulin demand without any need for external monitoring or injecting of insulin into the diabetic patient. The system provides for sensing glucose levels internally, and responding by stimulating either the pancreas or a transplant of pancreatic islets in order to enhance insulin production. The enhancing stimulation is delivered at a rate greater than the burst rate, or is otherwise controlled so that the depolarization burst constitutes a greater portion of each islet electrical cycle, thereby resulting in increased insulin production. In another embodiment, the system responds to a food intake signal, either externally or internally generated, by going through a time response algorithm to provide a stimulation-enhanced insulin response which simulates the natural response.

U.S. Pat. No. 6,135,978 to Houben et al., which is incorporated herein by reference, describes an implantable system and method for monitoring pancreatic beta-cell electrical activity in a patient in order to obtain a measure of a patient's insulin demand and blood glucose level. A stimulus generator is controlled to deliver stimulus pulses so as to synchronize pancreatic beta-cell depolarization, thereby producing an enhanced electrical signal which is sensed and processed. The insulin demand signal is used either to control delivery of insulin from an implanted insulin pump, or to control ongoing pancreatic stimulation of a form to enhance insulin production.

U.S. Pat. No. 6,832,114 to Whitehurst et al., which is incorporated herein by reference, describes techniques for introducing one or more stimulating drugs and/or applying electrical stimulation to the pancreas and/or nerve fibers innervating the pancreas to treat or prevent diabetes and/or to modulate pancreatic endocrine secretions.

Intragastric balloons for reducing the volume of the stomach to treat obesity have been described, including in the following patents and patent application publications, all of which are incorporated herein by reference: U.S. Pat. Nos. 4,416,267 and 4,899,747 to Garren et al., U.S. Pat. No. 4,694,827 to Weiner et al., U.S. Pat. No. 4,723,547 to Kullas et al., U.S. Pat. No. 4,739,758 to Lai et al., U.S. Pat. No. 5,234,454 to Bangs, U.S. Pat. No. 6,454,785 to De Hoyos Garza, U.S. Pat. No. 6,733,512 to McGhan, US Patent Application Publication 2003/0158569 to Wazne, US Patent Application Publication 2005/0004430 to Lee et al., PCT Publication WO 03/055420 to Lointier et al., PCT Publication WO 04/089262 to Paganon, and PCT Publication WO 87/00034 to Taylor.

U.S. Pat. No. 6,579,301 to Bales et al., which is incorporated herein by reference, describes an intragastric balloon device that includes a flexible bladder, a relatively rigid reservoir coupled to the bladder and adapted to hold a bladder inflation fluid, and an inflation/deflation system adapted to move or permit movement of the fluid from the reservoir and into the bladder. The intragastric balloon device is sized such that it may be positioned, in its entirety, into the stomach cavity. Various systems may be used to move or permit movement of the fluid. A control system is provided to automatically activate the inflation/deflation system. The automatic activation may be activated by a combination of one or more of a timer, the temperature of the stomach, the pressure in the stomach, the mechanical stress in the stomach, or another sensed condition.

U.S. Pat. No. 5,868,141 to Ellias, which is incorporated herein by reference, describes an endoscopic stomach insert for treating obesity in humans by reducing the desire for eating, comprising a base that is sized for passing through a human mouth and esophagus; a plurality of flexible blades coupled at one end thereof to the base and circumferentially arranged about the base central axis, where the blades are biased to extend substantially radially outward and downward from the base; and a retainer for releasably coupling the distal portions of the blades within close proximity to each other about the central axis of the base. The insert is thus adapted to be passed through the mouth and esophagus and into the stomach, and upon releasing the retainer within the stomach, the blades are biased to flare outwardly into the form of a dome-shaped cage, applying pressure to the stomach, and thus causing a sensation of fullness within the stomach and reducing the desire for eating.

PCT Publication WO 05/051486 to Mintchev, which is incorporated herein by reference, describes a method and apparatus for gastrointestinal motility control. An aspect of the invention is described as a method and apparatus for overriding the spontaneously existing gastrointestinal (GI) motility and producing artificial peristalsis completely asynchronously with the spontaneously existing mechanical phenomena in the GI tract, in a given GI organ, or in a portion thereof, using trains of external voltages with a wide range of frequencies (5-50,000 Hz), wide range of duty cycles (10-100%) and wide range of amplitudes (3-30 V peak-to-peak). Also described is a method and apparatus for producing preliminary externally controlled contractions in the sphincter region or regions of the GI organ or in a portion of it (for example, the pylorus in the stomach). The adjacent acetylcholine (ACh) patches in the vicinity of the sphincter region are exhausted due to the prolonged invoked contractions, so that the sphincter inevitably relaxes as a result. Additionally, apparatus invokes externally-controlled GI peristalsis after this sphincter relaxation is achieved, so that content is propelled through the sphincter. Also described is an implantable microsystem device to treat morbid obesity, which can make use of the same device.

PCT Publication WO 02/092165 to King, which is incorporated herein by reference, describes an embodiment in which apparatus is adapted for blocking activation of electrically excitable tissue, and more particularly for producing a desired effect by activating tissue at a first predetermined site and for reducing a corresponding undesired side effect by blocking activation of tissue or conduction of action potentials at a second predetermined site. The desired effect may be peristalsis of the patient's intestine; the undesired effect may be closure of the patient's ileocecal valve to the patient's colon. The first site may be the patient's intestinal wall smooth muscle, hypogastric plexus, or nerves to the patient's hypogastric plexus; and the second site may be the patient's ileocecal valve, mesenteric ganglia, dorsal root, spinal dorsal columns, or splanchnic nerves.

The following references, which are incorporated herein by reference, may also be of interest:
EP 1 392 393 B1 to King
U.S. Pat. No. 6,895,279 to Loeb et al.
U.S. Pat. No. 5,423,872 to Cigaina
US Patent Application Publication 2002/0072779 to Loeb
U.S. Pat. No. 6,571,127 to Ben-Haim et al.
U.S. Pat. No. 6,826,428 to Chen et al.
US Patent Application Publication 2003/0055467 to Ben-Haim et al.
US Patent Application Publication 2005/0085923 to Levine et al.
U.S. Pat. No. 6,684,105 to Cohen et al.
PCT Patent Publication WO 03/018118 to Cohen et al. and U.S. patent application Ser. No. 10/488,334 (granted as U.S. Pat. No. 7,734,355 to Cohen) in the national phase thereof
U.S. Pat. No. 6,993,391 to Flesler et al.
U.S. Pat. No. 7,006,871 to Darvish et al.
PCT Publication WO 06/018851 to Kliger et al.
PCT Publication WO 04/112563 to Ben-Haim et al.
PCT Publication WO 05/087310 to Harel et al.
US Patent Application Publication 2006/0085045 to Harel et al.

An article by Kalloo et al., entitled, "Flexible transgastric peritoneoscopy: A novel approach to diagnostic and therapeutic interventions in the peritoneal cavity," Gastrointest Endosc. 2004 July; 60(1): 114-7, which is incorporated herein by reference, describes testing of an endoscopic peroral transgastric approach to the peritoneal cavity in a porcine model in acute and long-term survival experiments. Transgastric peritoneoscopy was evaluated in 50-kg pigs. After upper endoscopy, the peritoneal cavity was accessed by needle-knife puncture of the gastric wall, followed by extension of the incision either with a pull-type sphincterotome or by balloon dilation. The peritoneal cavity was examined, and a liver biopsy specimen was obtained. The gastric wall incision was closed with clips. Twelve acute and 5 survival experiments were performed. Both techniques of gastric wall incision were without complication. The acute experiments demonstrated the technical feasibility of the approach. In the survival experiments, all pigs recovered and gained weight. The article concluded that the peroral transgastric approach to the peritoneal cavity is technically feasible and has the potential to be an alternative to laparoscopy and laparotomy.

An article by Sun et al., entitled, "Intestinal electric stimulation decreases fat absorption in rats: Therapeutic potential for obesity," Obes Res. 2004 August; 12(8):1235-42, which is incorporated herein by reference, describes a study investigating whether intestinal electric stimulation (IES) would reduce fat absorption and, thus, would be a potential therapy for obesity. Forty rats implanted with serosal electrodes and two jejunal cannulas were divided into 4 groups of 10 each: control (no stimulation), IES with long pulses, IES with trains of short pulses, and IES with trains of short pulses plus treatment with lidocaine. Jejunal transit and fat absorption of a 20-cm jejunal segment (between two cannulas) were investigated during a 45-minute period with or without IES. It was found that both methods of IES accelerated intestinal transit measured by recovery of phenol red and increased the percentage of triglycerides recovered from the distal cannula in comparison with the control group. IES with trains of short pulses was more effective than IES with long pulses in accelerating jejunal transit and reducing fat absorption. Neither of the two IES methods altered the output of fatty acids from the distal cannula. The effects of IES with trains of short pulses on the transit and fat absorption were partially abolished with the treatment of lidocaine. It was concluded that IES accelerates intestinal transit and reduces fat absorption, suggesting a therapeutic potential for obesity. IES with trains of short pulses was found to be more effective than IES with long pulses, and its effects are partially mediated by enteric nerves, jejunum.

An article by Giralt M et al., Neurogastroenterol Motil. April, 2000, 12(2):173-80, entitled, "Inhibition by CCK of ascending contraction elicited by mucosal stimulation in the duodenum of the rat," which is incorporated herein by reference, states that CCK released by intraluminal stimuli modifies duodenal activity, contributing to a decrease in gastric emptying. The article notes that the neural mechanisms by which CCK controls motility are not well known. The aim of this study was to investigate the interaction between CCK and the enteric nervous system through the study of the effects of CCK-8 on ascending excitation. Anaesthetized Sprague-Dawley rats were prepared with a strain-gauge sutured to the duodenum wall. An electrode holder was placed in the duodenum lumen to elicit ascending contraction. Electrical field stimulation of the duodenal mucosa (4 Hz, 0.6 ms, 30 V) induced an ascending excitation which was blocked by hexamethonium and atropine, but enlarged by L-NNA. CCK-8 blocked ascending excitation and an inhibition of the induced phasic activity was observed instead. In conclusion, CCK-8 blocked ascending contraction elicited by electrical field stimulation of duodenal mucosa by means of simultaneous activation of CCK-A and CCK-B receptors.

An article by Mukhopadhyay A K et al., Am J. Physiol. January, 1977, 232(1):E44-7, entitled, "Effect of cholecystokinin on myoelectric activity of small bowel of the dog," which is incorporated herein by reference, describes an experiment in which the effect of cholecystokinin on the myoelectric activity of the small intestine was determined in conscious dogs. Six animals were implanted with electrodes along the small intestine, and a cannula was placed in the stomach. A second cannula was inserted into the duodenum in three animals, and a pancreatic fistula was prepared in three animals. Recordings were made in the fasted state, during the intravenous infusion of either saline or cholecystokinin-octapeptide (CCK-OP), during the intraduodenal infusion of either saline or L-tryptophan, and during the fed state. CCK-OP disrupted the fasted pattern of myoelectric activity, caused a dose-dependent increase in spike potentials, and caused a dose-dependent increase in pancreatic protein secretion. Stimulation of myoelectric activity occurred at doses that produced submaximal protein secretion; however, the stimulation was not identical to that seen with feeding. Intraduodenal infusion of L-tryptophan increased pancreatic protein secretion, interrupted the fasted pattern of motility, and induced a pattern similar to that seen with feeding. The article concluded that CCK alters small intestinal motility and may play a role in the changes in small-bowel motility caused by the ingestion of food.

The following articles, which are incorporated herein by reference, may be of interest:

Bergman, R N et al., "The evolution of β-cell dysfunction and insulin resistance in type 2 diabetes," Eur J Clin Invest 32(Suppl. 3):35-45 (2002)

Chiasson, J L et al., "Prevention of type 2 diabetes: Insulin resistance and β-cell function," Diabetes 53(Suppl. 3):S34-S38 (2004)

Kahn S E, "The relative contributions of insulin resistance and beta-cell dysfunction to the pathophysiology of Type 2 diabetes," Diabetologia 46: 3-19 (2003)

Toyama M T et al., "Effect of ethanol on pancreatic interstitial pH and blood flow in cats with chronic pancreatitis," Annals of Surgery 225(2):223-228 (1997)

Liu S et al., "Therapeutic potential of duodenal electrical stimulation for obesity: Acute effects on gastric emptying and water intake," Am J Gastroenterol, 100(4):792-6 (2005).

SUMMARY OF THE INVENTION

In some embodiments of the present invention, a system for treating obesity and diabetes of a subject comprises a control unit, an eating sensor, an intragastric balloon, a nervous tissue stimulator, and a pancreatic stimulator. The nervous tissue stimulator comprises, for example, a stimulator adapted to stimulate the vagus nerve and/or a stimulator adapted to stimulate the enteric nervous system (ENS). Responsively to detection of eating by the eating sensor, the control unit drives the nervous tissue stimulator to stimulate the vagus nerve or the ENS so as to reduce appetite of the subject, and/or the pancreatic stimulator to stimulate pancreatic beta-cells to modulate (e.g., increase or decrease) insulin production and/or to otherwise regulate blood glucose. The system thus simultaneously addresses the interrelated factors of appetite control and beta-cell dysfunction found in many overweight diabetic subjects.

In some embodiments of the present invention, the pancreatic stimulator comprises one or more pancreatic electrodes, which are adapted to be inserted into a pancreatic duct, typically the main pancreatic duct. Typically, the pancreatic electrodes are implanted in the main pancreatic duct using an endoscope, which is advanced to the main pancreatic duct through the mouth, stomach, and duodenum. For some applications, the electrodes comprise ring electrodes, which are configured to substantially not block the flow of pancreatic juice through the pancreatic duct.

In some embodiments of the present invention, the eating sensor is adapted to be placed in the stomach or at another gastrointestinal tract site. For some applications, the eating sensor comprises one or more electrodes, configured to sense electrical activity in the stomach wall indicative of eating by the subject. In some embodiments, the eating sensor is incorporated into the intragastric balloon. For some applications, the electrodes are fixed to the surface of the balloon. Alternatively or additionally, the eating sensor comprises a pressure sensor, adapted to sense changes in pressure in the stomach that are indicative of eating by the subject.

For some applications, the nervous tissue stimulator is adapted to be placed in the duodenum and to stimulate tissue of the wall of the duodenum that innervates the vagus nerve and/or the ENS. For some applications, the control unit is adapted to be placed within the intragastric balloon. Alternatively, the control unit is adapted to be implanted elsewhere in the abdomen, or to be placed external to the subject's body.

There is therefore provided, in accordance with an embodiment of the invention, apparatus including:

one or more electrodes, adapted to be inserted in a pancreatic duct of a pancreas of a subject; and a control unit, adapted to drive the electrodes to apply a current to the pancreas, and to configure the current to modulate insulin production by beta cells of the pancreas.

In an embodiment, the electrodes include ring electrodes. For some applications, each of the ring electrodes includes a plurality of conductive segments, arranged around the ring electrode. Alternatively or additionally, the apparatus includes a stent, adapted to expand in the pancreatic duct, thereby opening the one or more electrodes in the pancreatic duct.

In an embodiment, the one or more electrodes are adapted to be inserted in a main pancreatic duct of the pancreas.

In an embodiment, the electrodes are configured to allow pancreatic juice to pass through the electrodes.

In an embodiment, the one or more electrodes include a plurality of electrodes, and the control unit is adapted to drive only a portion of the electrodes to apply the current at any given time. For example, the apparatus may include a set of wires connecting the control unit with the plurality of electrodes, and the control unit is adapted to send a multiplexed signal to the plurality of electrodes over the set of wires, and each of the plurality of electrodes includes a respective microchip that is adapted to drive the electrode to apply the current upon determining that the signal is addressed to the microchip.

There is further provided, in accordance with an embodiment of the invention, apparatus including:

one or more electrodes, adapted to be placed in contact with a wall of a lumen of a duodenum of a subject;

a control unit, adapted to drive the electrodes to apply a current to the wall of the duodenal lumen, and to configure the current to stimulate a vagus nerve of the subject or an ENS of the subject.

For some applications, the apparatus includes an eating sensor, and the control unit is adapted to drive the electrodes to apply the current responsively to a signal from the eating sensor indicative of eating by the subject.

For some applications, the control unit is adapted to (a) configure the current in accordance with a set of parameters for the current, the set of parameters including a pulse width of pulses of the current and a frequency of application of the pulses, and (b) select the set of parameters to be such as to enhance closure of a pylorus of the subject and to lower a level of glucose in blood of the subject. Alternatively or additionally, the control unit is adapted to (a) configure the current in accordance with a set of parameters for the current, the set of parameters including a pulse width of pulses of the current and a frequency of application of the pulses, and (b) select the set of parameters to be such as to enhance closure of a pylorus of the subject and to increase a level of insulin in blood of the subject.

For some applications, two of the one or more electrodes, when in contact with the wall, are mutually spaced by a distance that is greater than the spacing between any other two of the one or more electrodes, when in contact with the wall, and the distance is less than 3 cm.

For some applications, the control unit is adapted to (a) configure the current to include a plurality of pulses, and (b) set a frequency of application of the pulses to be at least 0.1 Hz. For some applications, the control unit is adapted to apply at least some of the pulses as biphasic pulses. Alternatively or additionally, the control unit is adapted to apply at least some of the pulses as monophasic pulses For some applications, the control unit is adapted to set the frequency to be at least 1 Hz, such as at least 3 Hz.

For some applications, the control unit is adapted to configure the current to include a plurality of pulses, and at least two consecutive ones of the pulses each have respective pulse widths that are less than 75 ms, such as less than 30 ms, e.g., less than 15 ms.

In an embodiment, the control unit is adapted to (a) configure the current to include a plurality of pulses, (b) set a frequency of application of the pulses to a desired frequency value, and (c) set pulse widths of at least two consecutive pulses to be less than a threshold pulse width, wherein a ratio of the threshold pulse width to the desired frequency value is less than 1000 ms/Hz, such as less than 100 ms/Hz, e.g., less than 10 ms/Hz.

In an embodiment, the control unit is adapted to configure the current to be sufficient to cause closure of a pylorus of the subject. For some applications, the control unit is adapted to configure the current to be sufficient to cause the closure of the pylorus via a nerve-mediated pathway, but to be insufficient to cause the closure of the pylorus via direct electrical stimulation of muscle tissue of the pylorus.

For some applications, the one or more electrodes include at least two electrodes adapted to be placed 2-5 cm from the pylorus, or adapted to placed within 1-2 cm of the pylorus. For some applications, all of the one or more electrodes are adapted to be placed 2-5 cm from the pylorus, or adapted to be placed 1-2 cm from the pylorus.

In an embodiment, the control unit is adapted to be placed in a gastrointestinal tract of the subject. For example, the control unit may be adapted to be placed in a stomach of the subject. Alternatively, the control unit is adapted to be implanted in the subject outside of the stomach, and to be wirelessly coupled to the electrodes. Further alternatively, the control unit is adapted to be placed outside of a body of the subject, and to be wirelessly coupled to the electrodes.

There is still further provided, in accordance with an embodiment of the invention, apparatus including:

an eating sensor, adapted to be placed in a body of a subject, and to generate a signal indicative of eating by the subject;

a vagal nerve stimulator or ENS stimulator, adapted to be placed in a gastrointestinal tract of the subject;

one or more pancreatic electrodes, adapted to be endoscopically inserted into a pancreas of the subject; and a control unit, adapted to receive the eating signal, and, responsively thereto, to drive the vagal nerve stimulator or ENS stimulator to apply a first current to a vagus nerve or ENS of the subject, and to drive the pancreatic electrodes to apply a second current to pancreatic beta-cells of the subject.

There is also provided, in accordance with an embodiment of the invention, apparatus including:

an eating sensor, adapted to be placed in a body of a subject, and to generate a signal indicative of eating by the subject;

a vagal nerve stimulator or ENS stimulator, adapted to be placed in a gastrointestinal tract of the subject;

one or more electrodes, adapted to be laparoscopically, endoscopically, or in another manner implanted at respective duodenal sites of the subject; and a control unit, adapted to receive the eating signal, and, responsively thereto, to drive the vagal nerve stimulator or ENS stimulator to apply a first current to a vagus nerve or ENS of the subject, and to drive the electrodes to apply a second current that modulates activity of pancreatic beta cells of the subject.

In an embodiment, the control unit is adapted to set the first current to have a frequency equal to at least 3 times a frequency of the second current.

In an embodiment, the apparatus includes an intragastric balloon, adapted to be placed in a stomach of the subject. For some applications, the intragastric balloon includes the eating sensor.

There is yet further provided, in accordance with an embodiment of the invention, a method including:

inserting one or more electrodes in a pancreatic duct of a pancreas of a subject;

driving the electrodes to apply a current to the pancreas; and configuring the current to modulate insulin production by beta cells of the pancreas.

In an embodiment, inserting includes inserting the one or more electrodes in a main pancreatic duct of the pancreas. Alternatively or additionally, inserting the electrodes includes endoscopically inserting the electrodes via a mouth of the subject.

There is also provided, in accordance with an embodiment of the invention, apparatus including:

one or more electrodes, adapted to be placed in contact with a wall of a lumen of a duodenum of a subject;

a control unit, adapted to drive the electrodes to apply a current to the wall of the duodenal lumen, and to configure the current to stimulate a site selected from the group consisting of: a vagus nerve of the subject, and enteric nervous system (ENS) tissue of the subject.

In an embodiment, the site includes the vagus nerve of the subject, and the control unit is adapted to configure the current to stimulate the vagus nerve.

In an embodiment, the site includes the ENS tissue of the subject, and the control unit is adapted to configure the current to stimulate the ENS tissue.

In an embodiment, the control unit is adapted to be placed in a gastrointestinal tract of the subject.

In an embodiment, the control unit is adapted to be placed in a stomach of the subject.

In an embodiment, the control unit is adapted to be implanted in the subject outside of the stomach, and to be wirelessly coupled to the electrodes.

In an embodiment, the control unit is adapted to be implanted in the subject outside of the stomach, and the apparatus includes wires configured to couple the control unit to the electrodes.

In an embodiment, the control unit is adapted to be placed outside of a body of the subject, and to be wirelessly coupled to the electrodes.

There is additionally provided, in accordance with an embodiment of the invention, apparatus including:

an eating sensor, adapted to be placed in a body of a subject, and to generate a signal indicative of eating by the subject;

a stimulator adapted to stimulate a site selected from the group consisting of: a vagus nerve of the subject and enteric nervous system (ENS) tissue of the subject, and adapted to be placed in a gastrointestinal tract of the subject;

one or more pancreatic electrodes, adapted to be endoscopically inserted into a pancreas of the subject; and a control unit, adapted to receive the eating signal, and, responsively thereto, to drive the stimulator to apply a first current to the selected site of the subject, and to drive the pancreatic electrodes to apply a second current to pancreatic beta-cells of the subject.

In an embodiment, the control unit is adapted to set the first current to have a frequency equal to at least 3 times a frequency of the second current.

In an embodiment, the apparatus includes an intragastric balloon, adapted to be placed in a stomach of the subject.

In an embodiment, the intragastric balloon includes the eating sensor.

There is yet additionally provided, in accordance with an embodiment of the invention, a method including:

inserting one or more electrodes in a pancreatic duct of a pancreas of a subject;

driving the electrodes to apply a current to the pancreas; and configuring the current to modulate insulin production by beta cells of the pancreas.

In an embodiment, inserting includes inserting the one or more electrodes in a main pancreatic duct of the pancreas.

In an embodiment, inserting the electrodes includes endoscopically inserting the electrodes via a mouth of the subject.

There is still additionally provided, in accordance with an embodiment of the invention, a method including:

inserting one or more helical electrodes into a duodenum of a subject;

expanding the one or more electrodes to establish electrical contact between the one or more electrodes and a wall of the duodenum;

driving a current through the one or more electrodes; and configuring the current to induce a contraction of the duodenum.

There is also provided, in accordance with an embodiment of the invention, a method including:

inserting a stent including one or more electrodes into a duodenum of a subject;

driving a current through the one or more electrodes; and configuring the current to induce a contraction of the duodenum.

There is further provided, in accordance with an embodiment of the invention, a method including:

driving a current into a duodenal site of a subject; and configuring the current to enhance satiety of the subject by stimulating enteric nervous system (ENS) tissue of the subject.

There is still further provided, in accordance with an embodiment of the invention, a method including:

driving a current into a duodenal site of a subject; and configuring the current to enhance satiety of the subject by elevating a blood level of cholecystokinin (CCK) of the subject.

There is yet further provided, in accordance with an embodiment of the invention, a method including:

driving a current into a duodenal site of a subject; and configuring the current to enhance satiety of the subject by elevating a blood level of GLP-1 of the subject.

There is also provided, in accordance with an embodiment of the invention, a method including:

placing first and second electrodes at respective first and second sites of a duodenum of a subject; and activating the electrodes to increase a blood insulin level of the subject.

In an embodiment, placing includes placing the electrodes such that a straight line connecting the electrodes passes through a pancreas of the subject.

In an embodiment, the method includes sensing an indication of the subject having eaten a meal, and activating the electrodes responsively thereto.

In an embodiment, In an embodiment, placing includes placing the first and second electrodes at least 5 cm apart.

In an embodiment, activating the electrodes includes applying a signal having an amplitude between 2 mA and 8 mA, and a frequency between 3 Hz and 20 Hz.

In an embodiment, applying the signal includes (a) applying the signal for less than 5 seconds, (b) withholding the signal for greater than 10 seconds, and (c) cycling between (a) and (b).

In an embodiment, the method includes driving a current into the duodenum configured to induce satiety in the subject.

In an embodiment, driving the current includes delaying gastric emptying.

In an embodiment, driving the current includes configuring the current to induce afferent vagal signaling that reduces eating by the subject.

In an embodiment, the method includes driving a current into the duodenum configured to induce contraction of the duodenum.

In an embodiment, driving the current includes configuring the current to induce peristalsis.

In an embodiment, driving the current includes increasing a rate of peristalsis.

In an embodiment, driving the current includes configuring the current to induce at least one migratory motor complex (MMC).

In an embodiment, the method includes timing the driving of the current such that the MMC occurs at a time earlier than a natural time of MMC occurrence.

There is additionally provided, in accordance with an embodiment of the invention, a method including:

placing first and second electrodes at respective first and second abdominal sites of a subject; and activating the electrodes to inhibit a level of effectiveness of a digestive juice.

In an embodiment, the digestive juice includes bile, and activating includes activating the electrodes to inhibit a level of effectiveness of the bile.

In an embodiment, the digestive juice includes pancreatic juice, and activating includes activating the electrodes to inhibit a level of effectiveness of the pancreatic juice.

In an embodiment, the first and second abdominal sites include first and second duodenal sites, and placing includes placing the electrodes at the first and second duodenal sites, such that a straight line connecting the electrodes passes through a pancreas of the subject.

There is yet additionally provided, in accordance with an embodiment of the invention, a method including:

driving a current between first and second electrodes at respective first and second sites, spaced by at least 5 mm, of a duodenum of a subject; and configuring the current to stimulate tissue in a longitudinal muscle layer of the duodenum.

There is still additionally provided, in accordance with an embodiment of the invention, a method, including:

driving a current between first and second electrodes at respective first and second sites, spaced by less than 5 mm, of a duodenum of a subject; and configuring the current to stimulate tissue in a circular muscle layer of the duodenum.

There is also provided, in accordance with an embodiment of the invention, apparatus, including:

a capsule adapted to be swallowed by a subject;

a sensor, adapted to be implanted within the subject, to detect proximity of the capsule to the sensor, and to generate a sensor signal responsively thereto; and a treatment unit, adapted to apply a treatment to the subject in response to receiving the sensor signal.

In an embodiment, the capsule includes a magnet.

In an embodiment, the capsule has a diameter of less than 2 mm.

In an embodiment, the treatment unit is adapted to apply a treatment that induces satiety of the subject.

In an embodiment, the treatment unit is adapted to apply a treatment that elevates blood insulin.

There is further provided, in accordance with an embodiment of the present invention, a method including:

applying a current to a wall of a lumen of a duodenum of a subject; and configuring the current to stimulate a site selected from the group consisting of: a vagus nerve of the subject, and enteric nervous system (ENS) tissue of the subject.

There is still further provided, in accordance with an embodiment of the present invention, a method including:

generating, from with a body of a subject, a signal indicative of eating by the subject;

placing, in a gastrointestinal tract of the subject, a stimulator adapted to stimulate a site selected from the group consisting of: a vagus nerve of the subject and enteric nervous system (ENS) tissue of the subject;

implanting one or more electrodes at respective duodenal sites of the subject; and receiving the eating signal, and, responsively thereto, driving the stimulator to apply a first current to the selected site of the subject, and driving the one or more electrodes to apply a second current that modulates activity of pancreatic beta cells of the subject.

The present invention will be more fully understood from the following detailed description of embodiments thereof, taken together with the drawings, in which:

DETAILED DESCRIPTION OF EMBODIMENTS

Figure 1:
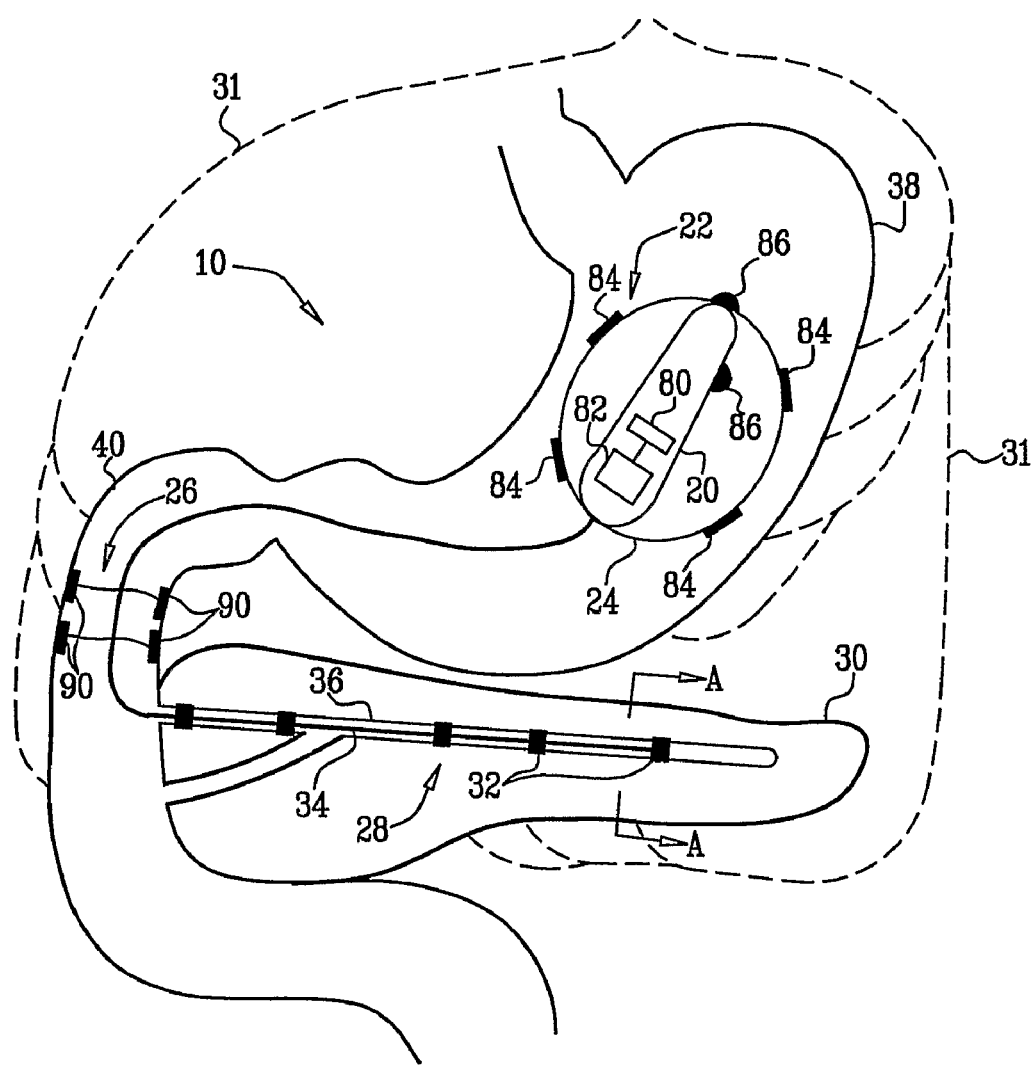
FIG. 1 is a schematic illustration of a system for treating obesity and diabetes, in accordance with an embodiment of the present invention.

FIG. 1 is a schematic illustration of a system 10 for treating obesity and diabetes, in accordance with an embodiment of the present invention. System 10 typically comprises a control unit 20, an eating sensor 22, an intragastric balloon 24, a tissue stimulator 26, and a pancreatic stimulator 28 implantable in a pancreas 30 of a subject. Responsively to detection of eating by eating sensor 22, control unit 20 drives tissue stimulator 26 to stimulate the vagus nerve or enteric nervous system (ENS) so as to reduce appetite, and/or pancreatic stimulator 28 to stimulate pancreatic beta-cells to modulate insulin production and/or to otherwise regulate blood glucose. (Dashed lines 31 symbolically represent vagal innervation of the upper gastrointestinal tract and pancreas.) It is noted that although some embodiments of the present invention are described with respect to tissue stimulator 26 applying its stimulation to nervous tissue, the scope of the present invention includes driving stimulator 26 to apply stimulation to muscle tissue, as well.

Control unit 20 is typically externally programmable following implantation to allow calibration or intermittent optimization of various signal parameters, such as duty cycle (e.g., number and/or timing of hours of operation per day), signal frequencies, and signal amplitudes. Similarly, external programming typically allows control of scheduling of various modes of operation of control unit 20 (e.g., glucose control, satiety inducement, and inducement of peristalsis or migrating motor complex (MMC)).

In an embodiment of the present invention, pancreatic stimulator 28 comprises one or more pancreatic electrodes 32, and at least one lead 34 that connects the electrodes. The electrodes are adapted to be inserted into a pancreatic duct of pancreas 30, typically a main pancreatic duct 36. Typically, pancreatic stimulator 28 is implanted in main pancreatic duct 36 using an endoscope (not shown), which is advanced to main pancreatic duct 36 through a mouth, a stomach 38, and a duodenum 40 of the subject. Typically, pancreatic stimulator 28 comprises between about 1 and about 10 pancreatic electrodes 32, such as between about 1 and about 4 electrodes. Typically, electrodes 32 comprise ring electrodes. For some applications, each ring electrode comprises a plurality of conductive segments, e.g., between 2 and 4, arranged around the ring electrode. For some applications, control unit 20 is adapted to drive pancreatic electrodes 32 to apply a current having a frequency of between about 0.5 and about 3 Hz. For some applications, pancreatic electrodes 32 comprise a material resistant to damage by the high pH of pancreatic juice, such as stainless steel 316L, titanium, or pure gold.

In an embodiment, control unit 20 balances, over the long term, the total positive current and the total negative current driven out of one or more of electrodes 32. Thus, for example, during a time period lasting over about 15 minutes, or over about 12 hours, the net current driven out of at least one of the electrodes is zero. It is hypothesized that for some applications, this charge balancing minimizes changes in pH that may be induced by non-balanced charge application.

For some applications, control unit 20 is adapted to drive only a portion of electrodes 32 at any given time, such as by cycling through the electrodes. Such non-constant stimulation by any one electrode typically reduces the risk of overworking pancreatic beta cells. For some applications, control unit 20 drives only a portion of the electrodes by sending a multiplexed signal to all of the electrodes over a set of wires. For example, control unit 20 may use time-division, frequency-division, or digital multiplexing. To enable such multiplexing, each electrode typically comprises a microchip that interprets whether the signal generated by control unit 20 is intended to cause the electrode to apply a current to pancreatic tissue in its vicinity.

In an embodiment, a substance is administered to the subject to counteract any destabilization of the pancreas caused by the insertion of pancreatic electrodes 32. For example, the substance may provide pH, enzymatic, and/or hormonal stabilization. For some applications, the substance is administered in the form of a pill, while for other applications, pancreatic electrodes 32 are coated with the substance. Alternatively, the substance is stored in balloon 24, and is driven or passively migrates into pancreatic duct through a tube coupled to the balloon.

Figure 2A:
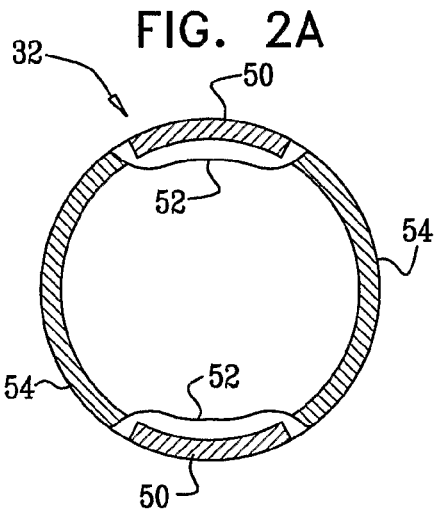
FIGS. 2A-C are schematic cross-sectional illustrations of configurations of pancreatic electrodes, in accordance with respective embodiments of the present invention.
Figure 2B:
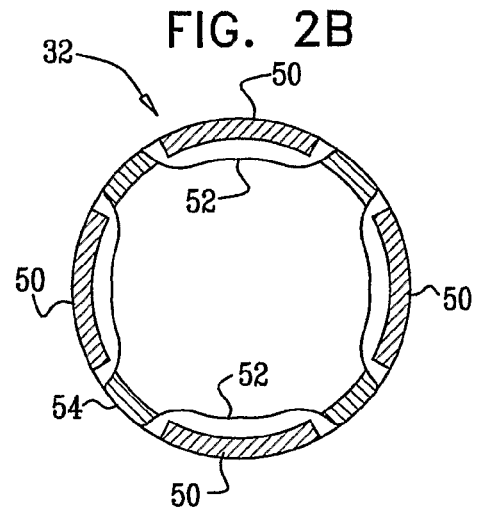
Figure 2C:
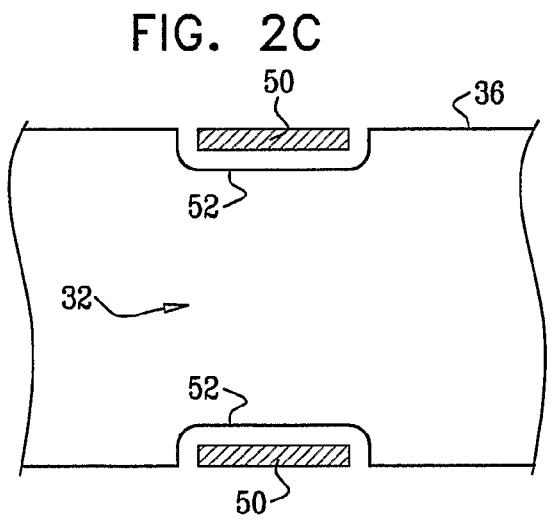

Reference is made to FIGS. 2A-C, which are schematic cross-sectional illustrations of configurations of pancreatic electrodes 32, in accordance with respective embodiments of the present invention. In these embodiments, pancreatic electrodes 32 comprise ring electrodes, which are configured to substantially not block the flow of pancreatic juice through main pancreatic duct 36. In the embodiment shown in FIG. 2A, pancreatic electrode 32 comprises two electrical contacts 50, one of which serves as a cathode and the other as an anode. For some applications, each one of contacts 50 intermittently serves as a cathode and intermittently serves as an anode. In the embodiment shown in FIG. 2B, the electrode comprises four electrical contacts 50, two of which typically serve as cathodes and the others as anodes. For some applications, each one of contacts 50 intermittently serves as a cathode and intermittently serves as an anode. For other applications, pancreatic electrodes 32 comprise three contacts, or a greater number of contacts, such as between 5 and 10 contacts (configurations not shown). In an embodiment, three or more, or even all, of the contacts are individually addressable by control unit 20.

Typically, each contact 50 comprises electrical insulation 52, which may comprise, for example, silicone. Pancreatic electrodes 32 additionally comprise a non-conductive structural support 54, which may, for example, comprise a mesh, such as a woven mesh. FIG. 2C shows a cross-sectional illustration of pancreatic electrode 32 as viewed from the side. As can be seen, contacts 50 and insulation 52 slightly protrude into main pancreatic duct 36 in this embodiment.

Figure 3A:
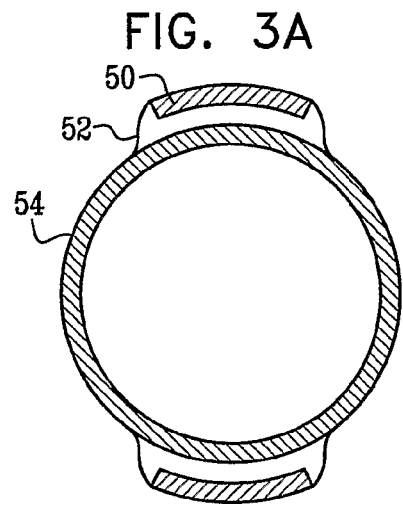
FIGS. 3A-C are schematic cross-sectional illustrations of additional configurations of pancreatic electrodes, in accordance with respective embodiments of the present invention.
Figure 3B:
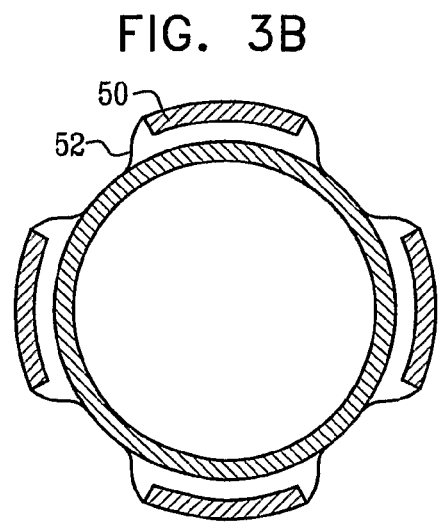
Figure 3C:
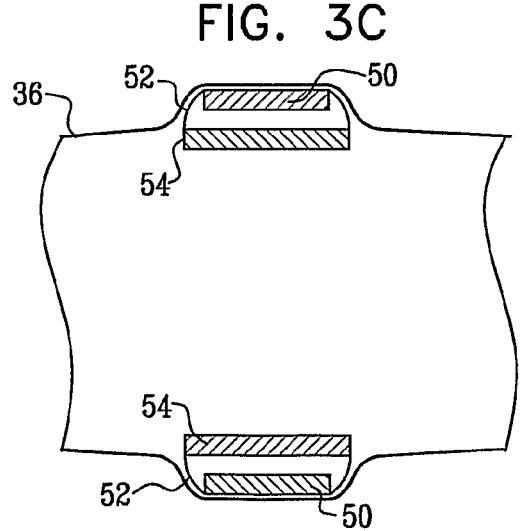

FIGS. 3A-C are schematic cross-sectional illustrations of additional configurations of pancreatic electrodes 32, in accordance with respective embodiments of the present invention. These configurations are similar to those described hereinabove with reference to FIGS. 2A-C, except that contacts 50 and insulation 52 protrude outward from support 54, rather than inward from the support. As a result, contacts 50 and insulation 52 slightly push into the wall of main pancreatic duct 36, as seen in FIG. 3C, leaving a greater cross-sectional area of the duct open than in the configurations shown in FIGS. 2A-C. In an embodiment of the present invention, pancreatic electrode 32 comprises an expandable stent, similar to a coronary stent, which is configured to open the electrode and push the contacts into the duct. Alternatively or additionally, a balloon or other tool is inserted into the electrode, inflated or otherwise expanded to open the electrode, and then removed from the electrode.

Figure 4:
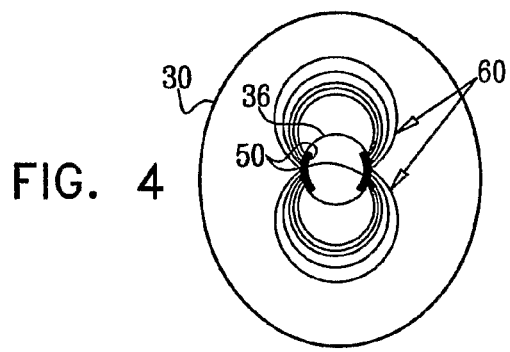
FIG. 4 is a schematic illustration of an electric field generated by a two-contact configuration of a pancreatic electrode, in accordance with an embodiment of the present invention.

FIG. 4 is a schematic illustration of hypothesized current flow 60 in a cross-section of pancreas 30, generated by a two-contact configuration of pancreatic electrode 32, in accordance with an embodiment of the present invention.

Figure 5:
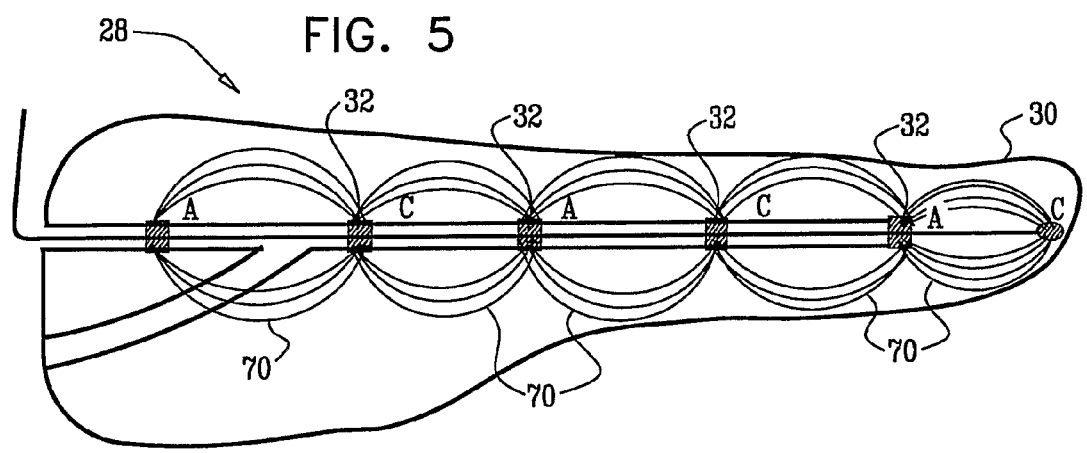
FIG. 5 is a schematic illustration of a configuration of a pancreatic stimulator, in accordance with an embodiment of the present invention.

Reference is made to FIG. 5, which is a schematic illustration of a configuration of pancreatic stimulator 28, in accordance with an embodiment of the present invention. In this embodiment, alternating pancreatic electrodes 32 each comprise a single cathode or anode (indicated in the figure by the letters C and A), such that a current flow 70 is created between adjacent electrodes (not necessarily simultaneously), as shown, or between non-adjacent electrodes. Pancreatic electrodes 32 are typically ring electrodes, and may be configured as described hereinabove with reference to FIGS. 2A-C or 3A-C, mutatis mutandis. Each of electrodes 32 comprises one or more contacts, which are typically inwardly insulated.

Reference is again made to FIG. 1. For some applications, control unit 20 is adapted to be placed within intragastric balloon 24. Alternatively, the control unit is adapted to be implanted elsewhere in the abdomen, or to be placed external to the subject's body. Control unit 20 typically comprises a microprocessor 80 and a power supply 82. The power supply typically comprises a battery, which, for some applications, is adapted to be inductively recharged from a power supply outside the subject's body.

In an embodiment of the present invention, system 10 comprises one or more gastric electrodes 84, adapted to be placed in stomach 38. For some applications, gastric electrodes 84 are coupled to a surface of intragastric balloon 24 (as shown), while for other applications, gastric electrodes 84 are adapted to be implanted in a wall of stomach 38 (configuration not shown).

In an embodiment of the present invention, eating sensor 22 is adapted to be placed in stomach 38. For some applications, eating sensor 22 comprises one or more of gastric electrodes 84, configured to sense electrical activity in the stomach wall indicative of eating by the subject.

In an embodiment of the present invention, control unit 20 is adapted to drive gastric electrodes 84 to stimulate the vagus nerve or ENS via stomach 38. For such stimulation, control unit 20 is typically adapted to drive electrodes 84 to apply a current having a frequency of between about 6 and about 30 Hz, such as between about 10 and about 15 Hz, e.g., about 12 Hz.

In an embodiment of the present invention, eating sensor 22 is incorporated into intragastric balloon 24. For some applications, gastric electrodes 84 of eating sensor 22 are fixed to a surface of the balloon, as mentioned above. Alternatively or additionally, eating sensor 22 comprises a pressure sensor 86, adapted to sense changes in pressure in stomach 38 that are indicative of eating by the subject. For some applications, pressure sensor 86 is placed outside the balloon, and is adapted to directly sense the pressure in the stomach. For other applications, pressure sensor 86 is placed in the balloon, and is adapted to sense the pressure in the balloon, which is indicative of the pressure in the stomach. In an embodiment, eating sensor 22 comprises a blood glucose sensor, which may be implanted in or external to the patient. In the latter instance, the glucose sensor is typically but not necessarily in wireless communication with control unit 20.

In an embodiment of the present invention, tissue stimulator 26 comprises one or more intestinal electrodes 90, which are adapted to be placed in a lumen of a gastrointestinal (GI) tract of the subject, such as in a lumen of duodenum 40, and to stimulate tissue of the wall of the GI tract that innervates the vagus nerve or the ENS. For some applications, the intestinal electrodes are placed against the wall of the duodenum, while for other applications the intestinal electrodes are implanted in the wall of the duodenum. For some applications, the control unit is configured to drive intestinal electrodes 90 to apply a current having a frequency of between about 10 and about 20 Hz. For some applications, the control unit configures the current to include a plurality of pulses, and sets a frequency and pulse width of the pulses such that a ratio of the pulse width to the frequency is less than 1000 ms/Hz. For example, the following pulse widths and frequencies, respectively, satisfy such a condition: (a) 90 ms and 0.1 Hz, (b) 9 ms and 0.1 Hz, (c) 9 ms and 1 Hz, (d) 5 ms and 1 Hz, and (e) 5 ms and 3 Hz. For some applications, tissue stimulator 26 utilizes techniques described in one or more of the vagal stimulation-related patents or patent application publications described hereinabove in the Background of the Invention. For some applications, system 10 is adapted to stimulate the vagus nerve or ENS using both gastric electrodes 84 and intestinal electrodes 90.

Figures 6A, 6B, 6C:
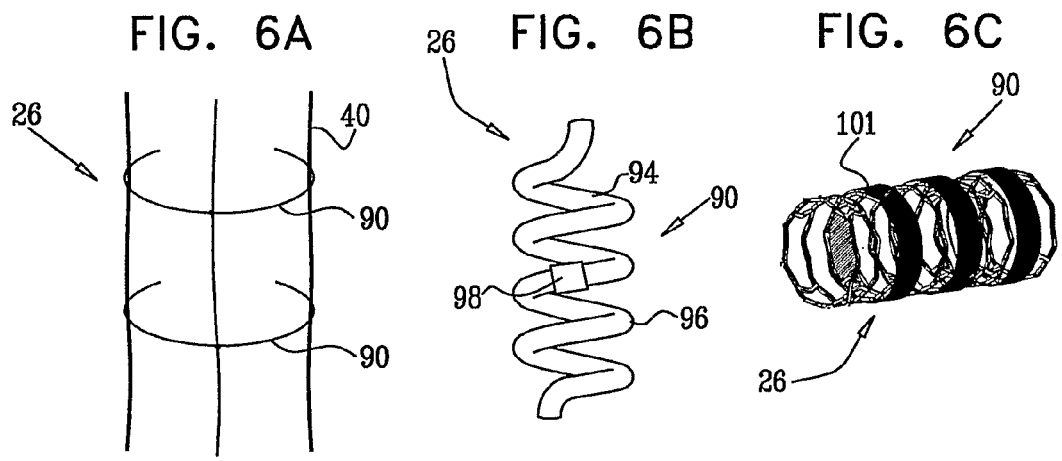
FIGS. 6A, 6B, and 6C are schematic illustrations of electrode configurations for use with a tissue stimulator, in accordance with respective embodiments of the present invention.

Reference is made to FIG. 6A, which is a schematic illustration of a configuration of electrodes 90 of tissue stimulator 26, in accordance with an embodiment of the present invention. In this embodiment, electrodes 90 are springy, and are adapted to be positioned against the wall of the lumen of duodenum 40. For some applications, tissue stimulator 26 comprises a stent, which is adapted to expand to push the electrodes into place. The stent is typically adapted to be temporary; for example, it may be dissolvable or removable.

FIG. 6B is a schematic illustration of tissue stimulator 26, in accordance with another embodiment of the present invention. In this embodiment, electrodes 90 comprise one or more helically-shaped electrodes, e.g., electrodes 94 and 96, which are held in place against the duodenal wall due to their uncompressed outer diameter being at least the inner diameter of duodenum 40. Alternatively or additionally, a small level of later-generated fibrosis is typically sufficient to hold the electrodes in place even if the duodenal diameter increases. For some applications, electrodes 90 or other electrodes described herein are secured in place using sutures, staples, hooks, or other securing apparatus known in the art of electrode implantation.

In an embodiment, electrodes 94 and 96 are individually addressable, and are electrically isolated by an isolator 98 (as shown) or are fabricated as physically separate units (configuration not shown).

FIG. 6C is a schematic illustration of tissue stimulator 26, in accordance with yet another embodiment of the present invention. In this embodiment, electrodes 90 comprise one or more ring electrodes 101 disposed on the outer surface of a stent 100. Alternatively or additionally, the body of the stent serves as an electrode. The stent is sized to fit into the patient's duodenum and to provide secure electrical contact between the ring electrodes and the duodenal wall.

Reference is made yet again to FIG. 1. Intragastric balloon 24 is adapted to be inflated in stomach 38, so as to reduce the volume of the stomach available for food storage, and thereby reduce appetite of the subject. In an embodiment of the present invention, intragastric balloon 24 is implemented using techniques described in one or more of the intragastric balloon-related patents or patent application publications described hereinabove in the Background of the Invention. For some applications, intragastric balloon 24 is adapted to remain constantly inflated after it has been inserted into stomach 38. Alternatively, the balloon is adapted to change shape and/or size after it has been inserted into the stomach, such as responsively to detection of eating or cessation of eating. In an embodiment, system 10 comprises the endoscopic stomach insert described in the above-mentioned U.S. Pat. No. 5,868,141, instead of or in addition to intragastric balloon 24.

In an embodiment, as generally described hereinabove, current is driven between two of pancreatic electrodes 32 into adjacent tissue, and/or between two of gastric electrodes 84 into adjacent tissue, and/or between two of intestinal electrodes 90 into adjacent tissue. Alternatively or additionally, current is driven between one of electrodes 32 and one of electrodes 84, so as to pass through tissue that is generally therebetween. Further alternatively or additionally, current is driven between one of electrodes 32 and one of electrodes 90, so as to pass through tissue that is generally therebetween. Still further alternatively or additionally, current is driven between one of electrodes 84 and one of electrodes 90, so as to pass through tissue that is generally therebetween.

As described hereinabove, for some applications, eating of the subject is detected, and current is driven into tissue of the subject in response thereto. Alternatively or additionally, the current is driven in response to blood glucose sensing, using implanted or external blood glucose sensors as are known in the art.

Figure 7:
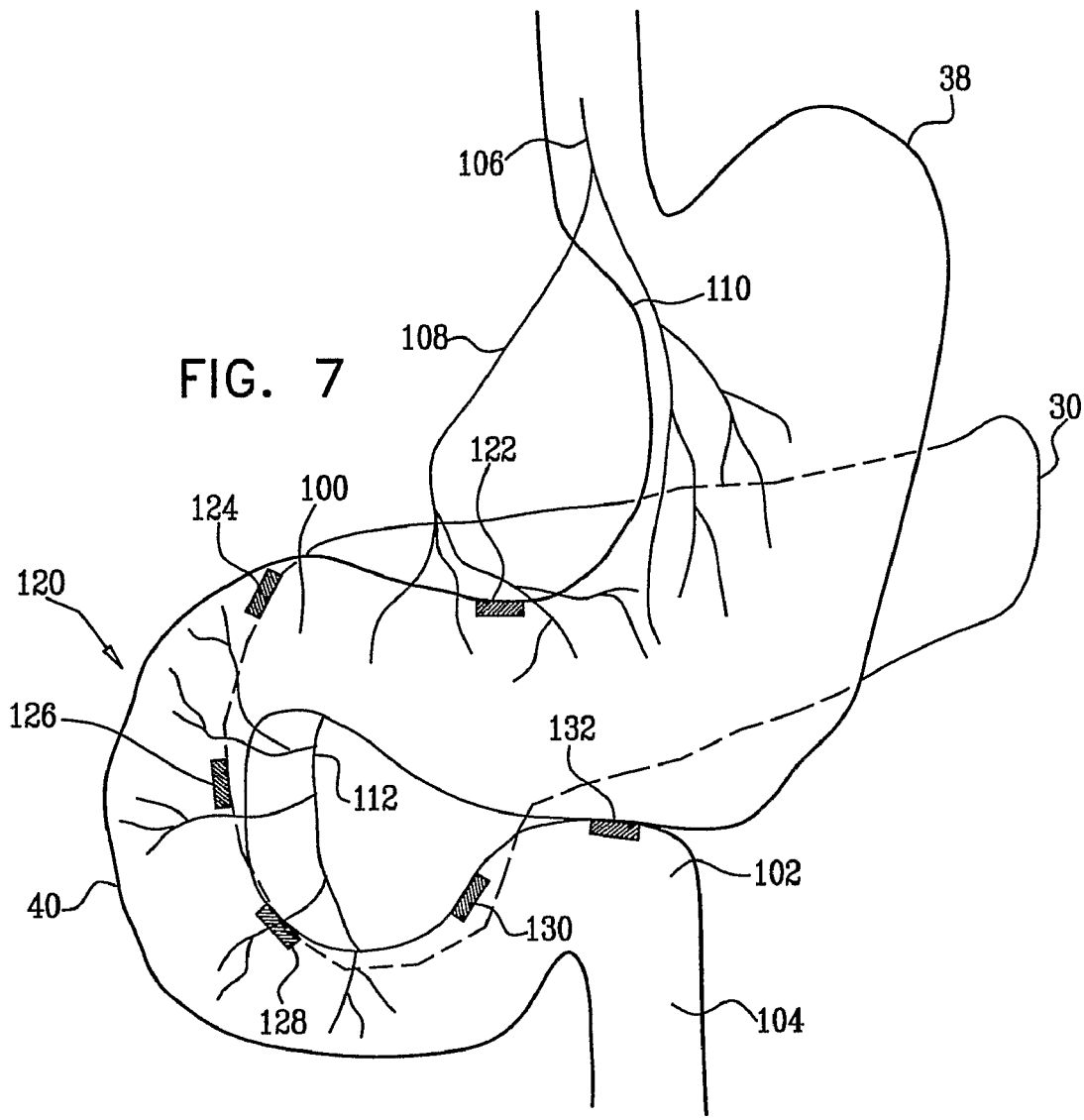
FIG. 7 is a schematic illustration of a stimulator, in accordance with an embodiment of the present invention.

FIG. 7 is a schematic illustration of a stimulator for modulating activity of the vagus nerve, activity of the ENS, activity of the endocrine pancreas, activity of the exocrine pancreas, and/or activity of the gastrointestinal tract, in accordance with an embodiment of the present invention. Techniques described hereinbelow with reference to FIG. 7 may be practiced in combination with techniques described hereinabove with reference to FIG. 1, as appropriate. A set 120 of one or more electrodes, e.g., comprising electrodes 122, 124, 126, 128, 130, and/or 132, is typically disposed within the duodenum or coupled thereto. For some applications, one or more of the electrodes (e.g., electrode 122) are disposed within stomach 38. Alternatively or additionally, one or more of the electrodes (e.g., electrode 132) are disposed at a more distal site, such as at duodenojejunal flexure 102. The electrodes in electrode set 120 may include electrodes as described with reference to FIG. 6, or, alternatively, other electrodes known in the art for placement at various sites of the gastrointestinal tract.

In an embodiment, two or more of the electrodes in electrode set 120 are coupled to control unit 20 (shown in FIG. 1 to be in the stomach, but alternatively disposed in the duodenum, subcutaneously, or within the peritoneum). Control unit 20 drives the electrodes to generate a signal that modulates activity of the pancreas by modulating secretion of a substance by the pancreas (e.g., insulin, glucagon, or pancreatic juice). Alternatively, the signal modulates another activity of pancreas 30. For some applications, electrodes from electrode set 120 are selected to modulate pancreatic activity based on their location within duodenum 40. For example, a current or a field may be driven or generated between electrode 122 and electrode 132. Other options, for example, include those shown in Table I that are marked by an X:

TABLE I

| from | to | | | | | |
|---|---|---|---|---|---|---|
|  | 122 | 124 | 126 | 128 | 130 | 132 |
| 122 | — | O | X | X | X | X |
| 124 | O | — | O | X | X | X |
| 126 | X | O | — | O | X | X |
| 128 | X | X | O | — | O |  |
| 130 | X | X | X | O | — | O |
| 132 | X | X | X |  | O | — |

The inventors hypothesize that by generating a current or field between two electrodes that are separated by a significant portion of pancreatic tissue (i.e., a straight line connecting the electrodes pass through the pancreas), the effect on the tissue of that current or field is typically greater than if that current or field were generated between two closely-adjacent electrodes.

For some applications, e.g., inducing a sensation of satiety, a current or field is generated between two electrodes that are marked by an "O" in Table I, in order to modulate ENS activity or vagus nerve activity in a branch of the vagus nerve near the two electrodes. In an embodiment, the current or field is applied at between about 3 and about 50 Hz, e.g., between about 3 and about 20 Hz. Alternatively or additionally, techniques and/or signal parameters described in U.S. Pat. No. 5,188,104 to Wernicke et al. are used or adapted for use in carrying out these applications of the present invention.

Table I is to be understood as an efficient protocol for modulating pancreatic, ENS, or vagus nerve activity. Nerve and pancreatic stimulation parameters described herein or in references cited in the Background section of this application, combined with other techniques described herein, are still generally effective even when applied not in accordance with the overall teaching of Table I.

In an embodiment, different subsets of electrode set 120 are activated depending on whether it is desired to modulate nervous activity (e.g., vagus nerve activity or ENS activity) or whether it is desired to modulate pancreatic activity. For example, a fixed schedule or a schedule based on sensing patient eating or blood glucose level may be used to determine when to modulate ENS or vagus nerve activity and when to modulate pancreatic activity. In some patients, pancreatic and nervous activity are modulated simultaneously. Alternatively, in a given patient the stimulator is configured to modulate nervous activity and substantially not to directly modulate pancreatic activity, or to modulate pancreatic activity and substantially not to directly modulate nervous activity.

Typically, electrode set 120 is implanted endoscopically. The electrodes may be on the inner wall of the gastrointestinal tract (as shown), within the tissue of the gastrointestinal tract, or protruding from or near the duodenum. Alternatively or additionally, one or more of the electrodes (e.g., electrode 132) is passed from within duodenum 40 to make contact with or penetrate pancreas 30. Alternatively or additionally, some or all of the electrodes in electrode set 120 are implanted laparoscopically. For example, the electrodes may be placed on the inner wall of the gastrointestinal tract (as shown), within the tissue of the gastrointestinal tract, or protruding from or near the duodenum. Alternatively or additionally, one or more of the electrodes is laparoscopically placed in contact with or caused to penetrate pancreas 30.

The electrodes may be intended for chronic or acute use, as appropriate for a given patient. For some applications, the electrodes are coupled to a tube that is placed in acute or chronic contact with the duodenum. In an embodiment, the tube is removed after a treatment, e.g., after two weeks to one year. In an embodiment, techniques described herein are combined with techniques described in the above-cited US Patent Application Publication 2005/0085923 to Levine, which is incorporated herein by reference. For example, electrode set 120 may be fixed to a sleeve or other apparatus such as is described in the Levine publication. For purposes of some embodiments of the present invention, the sleeve or other apparatus described in Levine may be adapted to reduce absorption of food calories into the patient's bloodstream (as described in Levine). Alternatively, the sleeve is not so adapted, but instead provides structural support for electrode set 120.

In embodiments in which a sleeve is provided for mounting the electrodes, as well as in embodiments in which no such sleeve is provided, electrode set 120 is typically disposed longitudinally along duodenum 40. Alternatively, one or more electrodes are located at only a single longitudinal site of the gastrointestinal tract. For some applications, a plurality of electrodes or a ring electrode is placed at each longitudinal site.

In an embodiment, the signal applied through electrode set 120 is configured to modulate exocrine activity of the pancreas, for example by modulating the (a) secretion, (b) level of activity, or (c) rate of breakdown of enzymes or other components in a digestive juice such as bile or pancreatic juice. Regulation of (a), (b), and/or (c) regulates the effect of the digestive juice on digestion. For some applications, in order to reduce the secretion of bile, one or more electrodes are placed within a bile duct, or on or near the liver. Alternatively or additionally, one or more electrodes are placed in or adjacent to a bile duct or a pancreatic duct, and driven to apply a field which breaks down enzymes in bile or pancreatic juice, or otherwise deactivates at least a portion of the enzymes. For example, the field may be tuned to a resonance frequency of one of the enzymes, and cause a heat-related change in structure of the enzyme. Further alternatively or additionally, one or more electrodes within or coupled to the duodenum are driven to apply a field that disrupts the ability of an enzyme to catalyze a biochemical reaction, e.g., by increasing a level of vibration of a portion of the enzyme and thereby inhibiting transient binding of a substrate to the active site of the enzyme.

Thus, for some applications, the effect of the digestive juice is reduced in order to render less efficient the breakdown of partially-digested food in the duodenum, and thereby reduce the body's absorption of calories from the food. As appropriate, this embodiment may be practiced in conjunction with other embodiments described herein for increasing the rate of passage of partially-digested food through the duodenum.

For some applications, control unit 20 drives electrode set 120 to apply a signal to duodenum 40 configured to induce satiety by elevating blood levels of GLP-1 and/or cholecystokinin (CCK).

In an embodiment, electrode set 120 is configured to induce a migrating motor complex (MMC) or one or more peristaltic waves in the duodenum, in order to reduce the time that absorbable food calories are resident in the duodenum. In this manner, at least some of the food calories that would otherwise have been absorbed through the duodenum into the bloodstream are instead passed through the gastrointestinal tract and passed as stool. As appropriate, techniques described in the above-cited article to Sun et al. may be adapted for use in this embodiment for stimulating the duodenum.

Typically, the MMC or peristaltic waves are induced in accordance with a schedule, for example so as to reduce caloric uptake from the duodenum by 25%, 50%, 75%, or almost 100%. For some applications, the caloric uptake is reduced based on a relationship between an actual weight of the patient and a desired weight of the patient. Alternatively, the schedule of the MMC or peristaltic waves is such as to reduce overall daily duodenal caloric uptake by a high value during a given week of operation, and by a lower value during a subsequent week of operation. Further alternatively, other techniques described herein are practiced more intensively while the patient has a high body weight, and progressively less intensively as the patient's weight decreases.

In an embodiment, induction of an MMC or peristaltic waves is timed in order to allow a detected meal to remain in the duodenum for a desired amount of time (e.g., about 1-10 minutes), and to be passed out of the duodenum at a time that is earlier than would occurred in the absence of the induction of the MMC or peristaltic waves. Alternatively, the MMC or peristalsis is initiated a predetermined or programmed time after detection of initiation of a meal (e.g., about 5-20 or 20-60 minutes thereafter). For some applications, the induction of the MMC or peristalsis is initiated in response to a blood glucose level of the patient in addition to an indication of absorbable food calories being present in the duodenum.

In an embodiment, the induction of the MMC or peristalsis is initiated upon detection or within 5, 15, or 30 minutes of the opening of the pylorus that allows expulsion of stomach contents into the duodenum. Typically, the opening of the pylorus is relatively small (e.g., several millimeters), and its opening is detected by electromyographic (EMG) analysis by control unit 20 of physiological electrical activity sensed by an electrode on the pylorus. Techniques for identifying a change in state of a muscle using EMG analysis are known in the art. Alternatively, other sensors adapted to sense pyloric opening and closing may be used, such as an acceleration sensor, a strain gauge, or an ultrasound sensor.

Alternatively or additionally, induction of the MMC or peristalsis is initiated in response to a detection of the occurrence of segmentation of the duodenum; the induced MMC or peristalsis typically terminates the segmentation process. For some applications, segmentation is detected responsively to a pattern of electrical activity along the duodenum that is measured by electrode set 120 and analyzed by control unit 20. Although electrical activity associated with segmentation is markedly different from that associated with peristalsis, a 6-24 or 24-72 hour calibration period for each patient may be provided to optimize the ability of control unit 20 to differentiate between segmentation and peristalsis in a particular patient. Alternatively, preprogrammed values associated with segmentation and peristalsis in a given patient population are incorporated into control unit 20.

In an embodiment, instead of or in addition to sensing electrical activity to identify the onset of segmentation, other sensors in the duodenum are used, such as acceleration sensors, strain gauges, or ultrasound sensors. As described above, these sensors identify when the process of segmentation has been initiated. Regardless of the type of sensor used, in these embodiments detection of segmentation serves as a trigger for initiating the induction of the MMC or peristalsis, so as to minimize the enhanced absorption of food calories caused by segmentation.

Alternatively, induction of the MMC or peristalsis is practiced not in response to any sensed event. For example, the MMC or peristalsis may be artificially initiated every 20 minutes during one or more periods every day (e.g., 5 am-2 pm and 4 pm-8 pm; or during pseudo-random periods not known to the patient), or for 5 minutes during every 30 minute period. In an embodiment, induction of the MMC or peristalsis is inhibited when the patient is asleep.

In one embodiment, peristalsis is induced by sequentially activating successive electrodes in electrode set 120, so as to contract duodenal muscle tissue and cause the contents of the duodenum to move distally. In another embodiment, a small number of electrodes located within a relatively small, typically proximal region of the duodenum are activated, and these "pace" the duodenum, inducing a peristaltic wave. Typically, the pacing rate is about 5% to about 50% faster than a physiological rate of peristaltic waves.

For some applications, electrodes that are mutually-spaced on the duodenum by more than about 5 mm (e.g., more than about 2 mm or more than about 7 mm) are driven to apply a current therebetween that, because of the interelectrode distance, penetrates the inner, circular muscle layer of the duodenum, and has a substantial excitatory effect in the outer, longitudinal muscle layer of the duodenum. Since the longitudinal muscle layer is largely responsible for peristalsis and the circular layer is largely responsible for mixing duodenal contents with digestive juice, this electrode arrangement tends to favor enhanced peristalsis over enhanced mixing of duodenal contents (relative to the result attained with electrodes spaced more closely together), and thereby inhibits calorie absorption.

Alternatively or additionally, electrodes that are mutually-spaced on the duodenum by less than about 5 mm (e.g., less than about 2 mm or less than about 4 mm) are driven to apply a current therebetween that, because of the interelectrode distance, largely remains within the inner, circular muscle layer of the duodenum, and has less effect on the outer, longitudinal muscle layer of the duodenum than would be attained with electrodes spaced further apart. Typically, this current is configured to inhibit muscle contraction, using signal protocols known in the art, and thereby reduce the level of mixing of duodenal contents and reduce calorie absorption.

In an embodiment, techniques described herein are combined with techniques described in the above-cited article by Liu et al. (2005), in order to delay gastric emptying and thus increase satiety.

Figure 8:
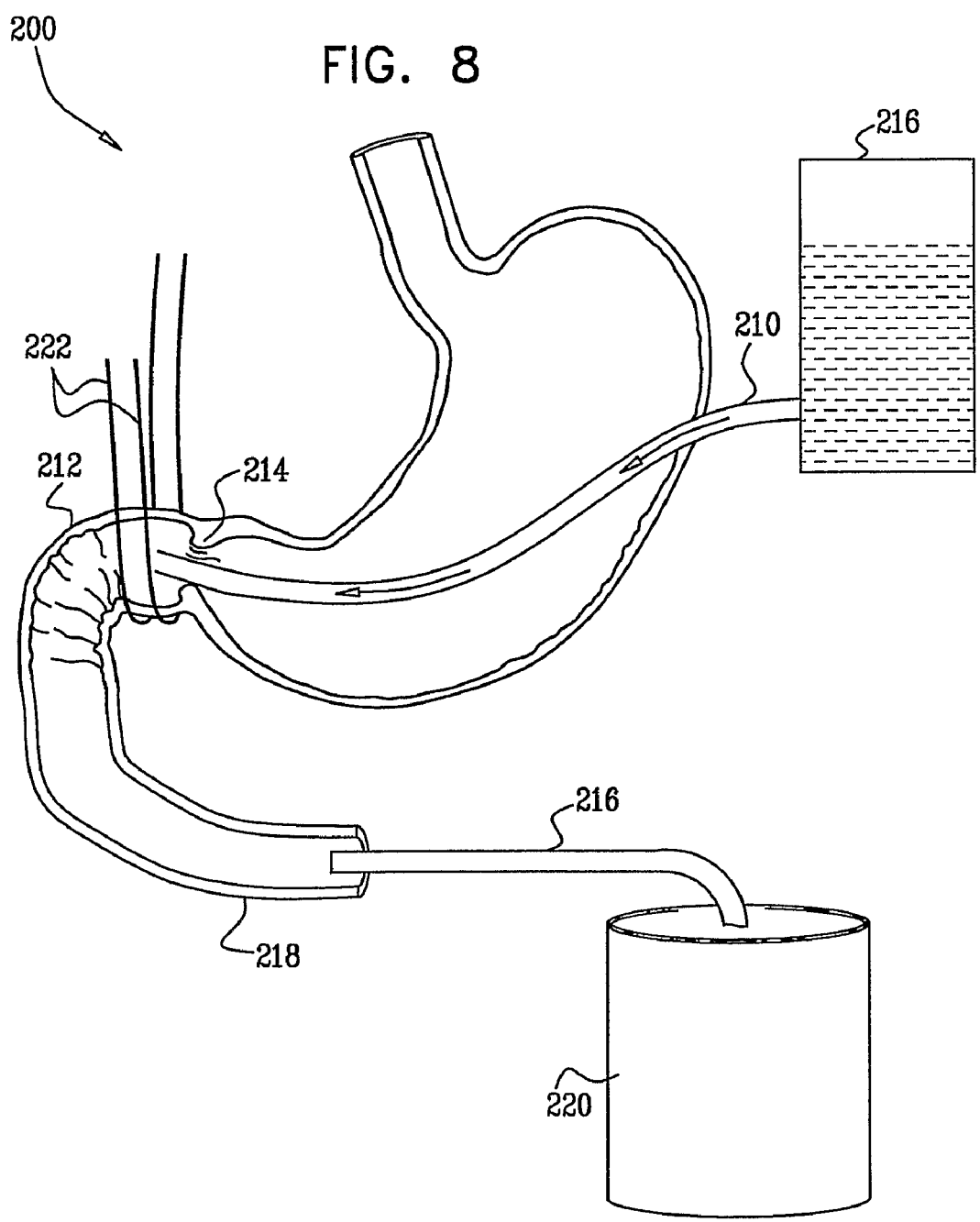
FIG. 8 is a schematic illustration of an experimental setup for studying the effect of intestinal electrical stimulation on duodenal nutrient flow in rats, in accordance with an embodiment of the present invention.

FIG. 8 is a schematic illustration of an experimental setup 200 for studying the effect of intestinal electrical stimulation on duodenal nutrient flow in rats, in accordance with an embodiment of the present invention. Each of the rats was anaesthetized by isoflurane, and the abdomen was opened by midlaparotomy. A first cannula 210 was inserted about 1 cm into a proximal portion 212 of the duodenum through a pylorus 214, and was connected to a water reservoir 216 located outside of the rat's body. A second cannula 216 was inserted into a distal portion 218 of the duodenum, and was connected to a tube 220 (Eppendorf AG), for collecting and measuring (by weighing) outflow from the duodenum. The length of the portion of the duodenum between the two cannulas was about 7 cm. The placement of first cannula 210 in the duodenum past pylorus 214 enabled the measurement of flow through the duodenum free of any effect the electrical stimulation may have had on the pylorus or gastric emptying. Two cardiac pacing wire electrodes 222 were placed about 5-10 mm apart around proximal portion 212 of the duodenum, about 1 cm from pylorus 214.

Figure 9:
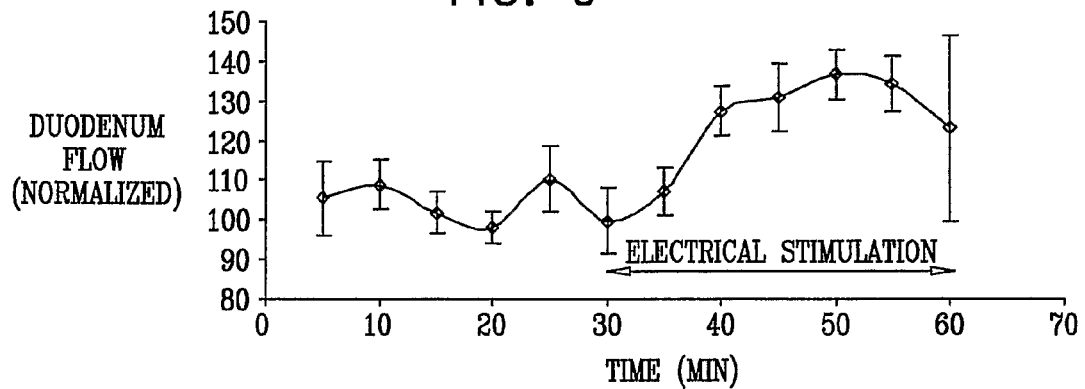
FIG. 9 is a graph showing experimental results obtained in an experiment performed on rats using the setup described hereinabove with reference to FIG. 8, in accordance with an embodiment of the present invention.

FIG. 9 is a graph showing experimental results obtained in an experiment performed on five rats using the setup described hereinabove with reference to FIG. 8, in accordance with an embodiment of the present invention. The graph reflects averaged results from the five rats. During a control period beginning at about four minutes and concluding at about 30 minutes, water from reservoir 216 was pumped into first cannula 210 at a constant rate. As can be seen in the graph, normalized flow exiting the duodenum via second cannula 216 was stable during this control period. During a stimulation period beginning at about 30 minutes and concluding at about 60 minutes, water continued to be pumped into first cannula 210 at the same constant rate, and electrodes 222 were driven to apply a biphasic electrical signal to the duodenum for 500 ms once every 4 seconds. The signal had a phase duration of 7 ms, a single-phase amplitude of 3-5 mA (i.e., 6-10 mA peak-to-peak), and a frequency of 30 Hz. As can be seen in the graph, the flow exiting the duodenum during electrical stimulation was about 40% greater than the flow during the control period.

Figure 10:
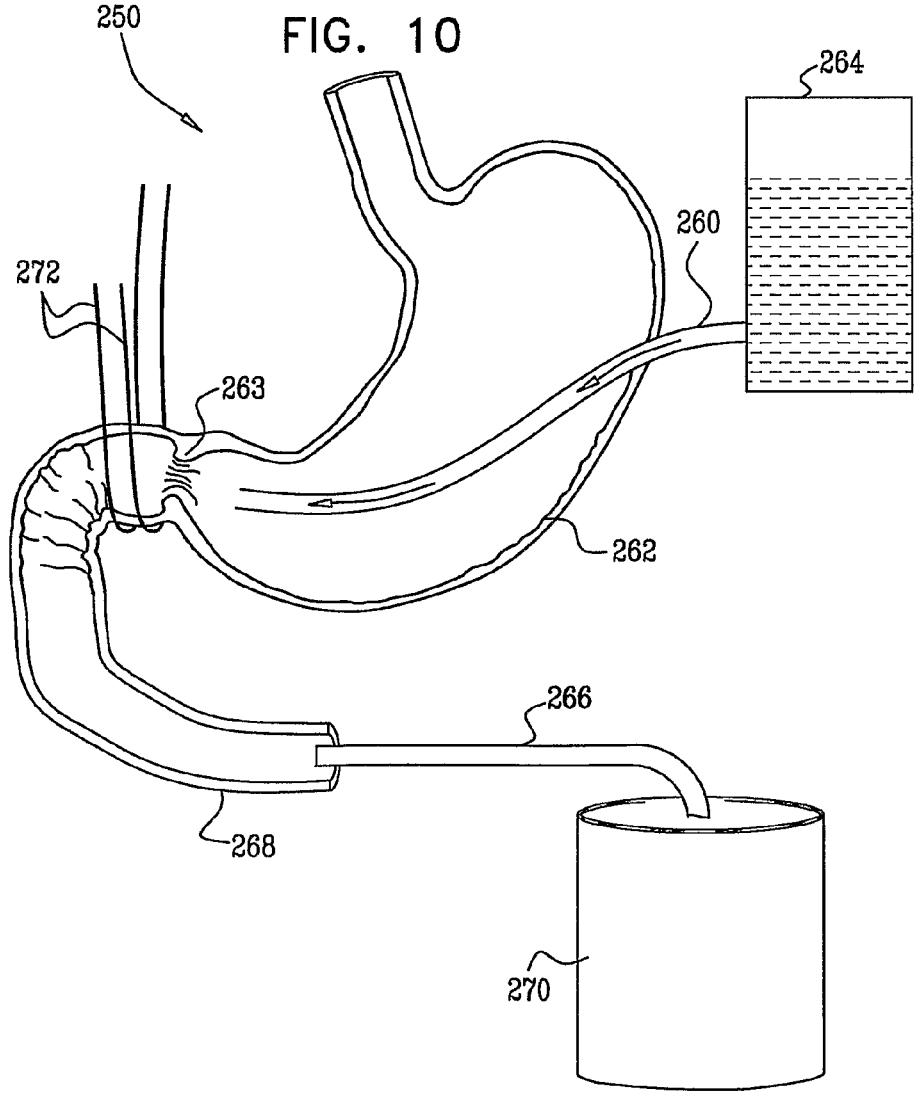
FIG. 10 is a schematic illustration of an experimental setup for studying the effect of intestinal electrical stimulation on gastric emptying in rats, in accordance with an embodiment of the present invention.

FIG. 10 is a schematic illustration of an experimental setup 250 for studying the effect of intestinal electrical stimulation on gastric emptying in rats, in accordance with an embodiment of the present invention. Each of the rats was anaesthetized by isoflurane, and the abdomen was opened by midlaparotomy. A first cannula 260 was inserted into a stomach 262 of the rat, and placed about 5-10 mm from a pylorus 263. The cannula was connected to a water reservoir 264 located outside of the rat's body. A second cannula 266 was inserted into a distal portion 268 of the duodenum, and was connected to a tube 270 (Eppendorf AG), for collecting and measuring (by weighing) outflow from the duodenum. Two cardiac pacing wire electrodes 272 were placed about 5-10 mm apart around proximal portion 212 of the duodenum, about 1 cm from pylorus 263.

Figure 11:
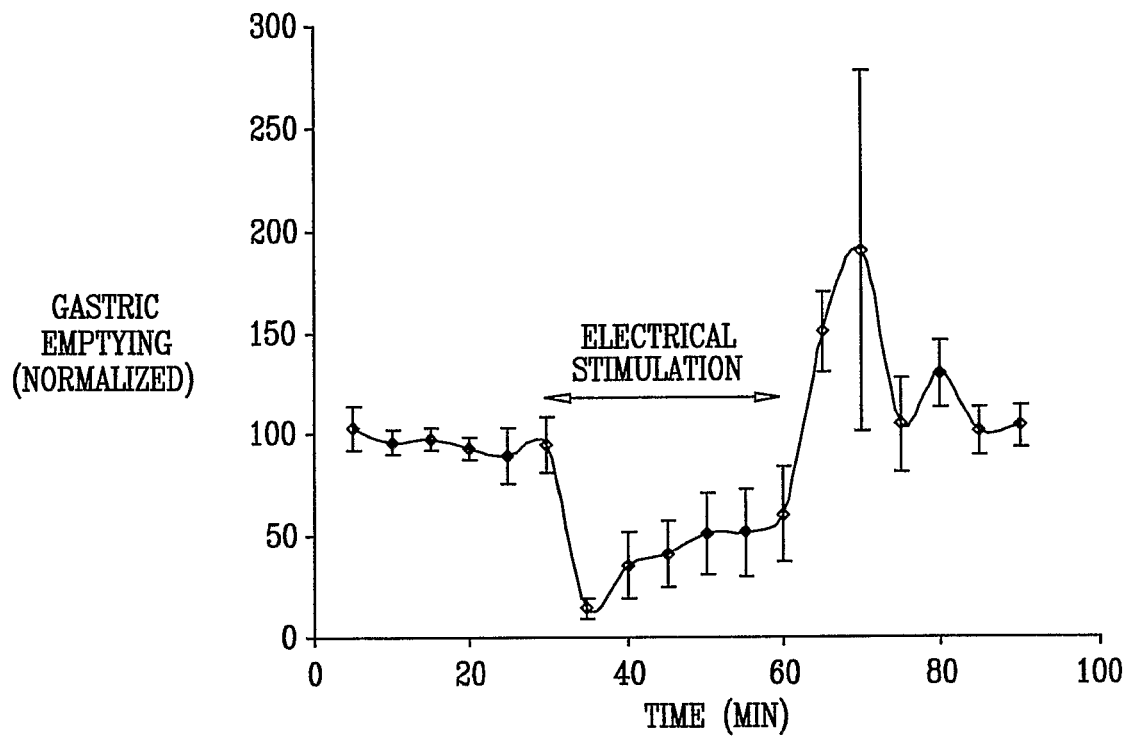
FIGS. 11 and 12 are graphs showing experimental results obtained in an experiment performed on rats using the setup described hereinabove with reference to FIG. 10, in accordance with respective embodiments of the present invention.

FIG. 11 is a graph showing experimental results obtained in an experiment performed on three rats using the setup described hereinabove with reference to FIG. 10, in accordance with an embodiment of the present invention. The graph reflects averaged results measured during five repetitions of the experiment performed on the three rats. During a first control period beginning at about four minutes and concluding at about 30 minutes, and a second control period beginning at about 60 minutes and concluding at about 90 minutes, water from reservoir 264 was pumped into first cannula 260 at a constant rate. As can be seen in the graph, normalized flow exiting the duodenum via second cannula 266 was stable during the first control period, and generally stable during the second control period. During a stimulation period beginning at about 30 minutes and concluding at about 60 minutes, water continued to be pumped into first cannula 260 at the same constant rate, and electrodes 272 were driven to apply a biphasic electrical signal to the duodenum for 500 ms once every 4 seconds. The signal had a phase duration of 7 ms, an amplitude of 3-5 mA, and a frequency of 30 Hz. As can be seen in the graph, the flow exiting the duodenum during the first 5 minutes of electrical stimulation was about 85% lower than the flow during the first control period, and remained suppressed throughout the stimulation period, indicating that gastric emptying was substantially reduced by the stimulation. The inventors hypothesize that this delayed gastric emptying was directly caused by closing of the pylorus because of the electrical stimulation of the duodenum.

Figure 12:
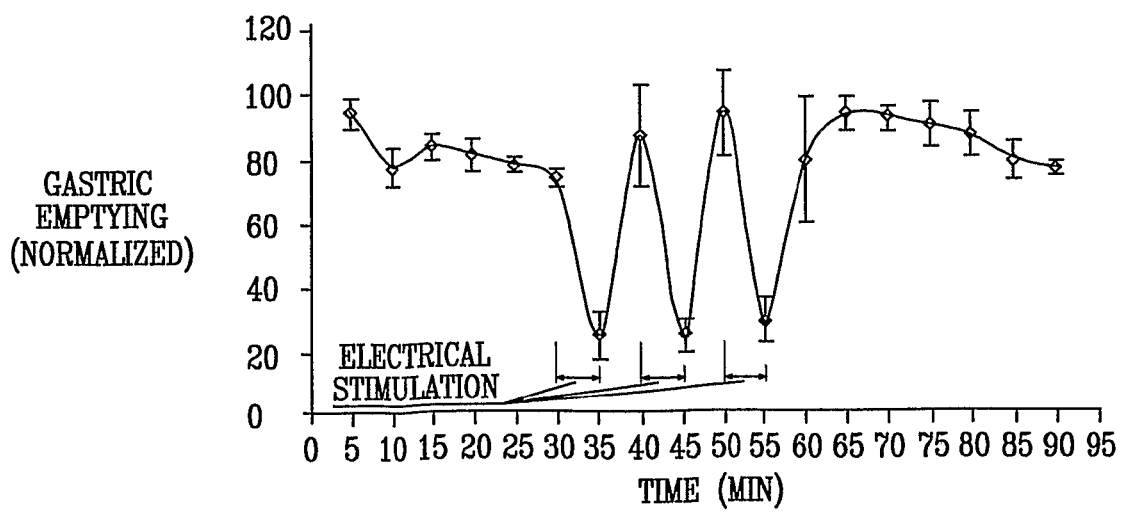

FIG. 12 is a graph showing experimental results obtained in an experiment performed on five rats using the setup described hereinabove with reference to FIG. 10, in accordance with an embodiment of the present invention. This experiment was performed using the same setup and stimulation parameters as those used in the experiment described hereinabove with reference to FIG. 11. As can be seen in the graph, short stimulation periods, each of which had a duration of five minutes, caused delayed gastric emptying. Furthermore, upon cessation of electrical stimulation after each stimulation period, baseline gastric emptying was quickly restored. These results indicate that the duodenal electrical stimulation closely controlled gastric emptying, and that the reduced gastric emptying appears to be fully reversible.

In an embodiment of the present invention, intestinal electrical stimulation is applied, such as using techniques described herein, to induce acute delayed gastric emptying by closing the pylorus. Such delayed gastric emptying generally induces satiety during a meal, and thus helps obese patients eat less, resulting in weight loss.

Figure 13:
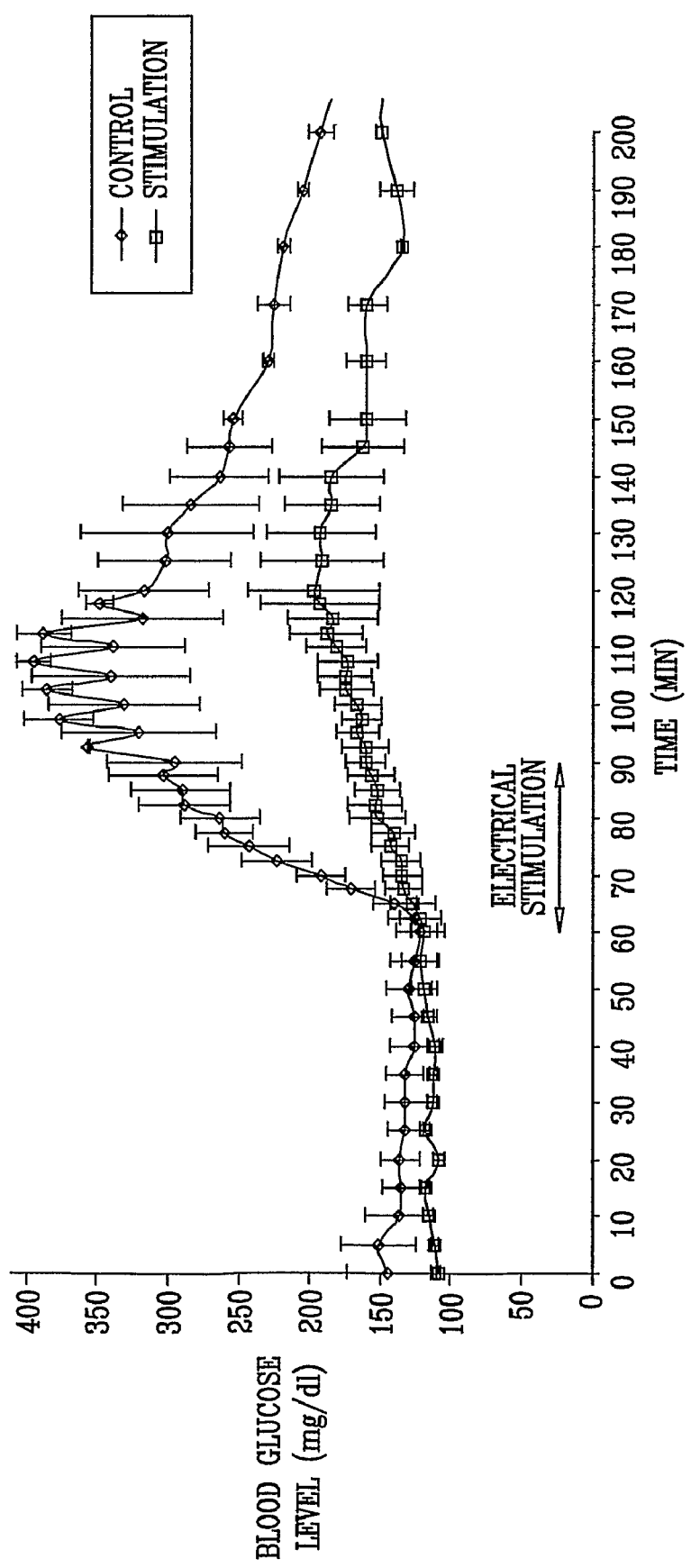
FIG. 13 is a graph showing experimental results obtained in an experiment studying the effect of intestinal electrical stimulation on nutrient absorption in rats, in accordance with an embodiment of the present invention.

FIG. 13 is a graph showing experimental results obtained in an experiment studying the effect of intestinal electrical stimulation on nutrient absorption in rats, in accordance with an embodiment of the present invention. The experiment was performed three times. Each time, a first rat received duodenal electrical stimulation, and a second rat served as a control. The graph reflects averaged results for the three stimulation rats and the three control rats. Each of the stimulation rats was anaesthetized by isoflurane, and the abdomen was opened by midlaparotomy. Two cardiac pacing wire electrodes were placed about 5-10 mm apart around a proximal portion of the duodenum, about 1 cm from the pylorus. The control rats were not implanted with electrodes. Blood samples were taken from the tail, and blood glucose level was measured by a glucometer (Accu-check Active, Roche).

In both the control and stimulation rats, during a 60-minute fasting period, blood glucose levels were measured every five minutes. At 60 minutes in the control rats and 61 minutes in the stimulation rats, glucose solution (2.5 cc, 50%) was injected in the stomach. In the stimulation rats, during a stimulation period beginning at about 60 minutes and concluding at about 90 minutes, the electrodes were driven to apply a biphasic electrical signal to the duodenum for 500 ms once every 4 seconds. The signal had a phase duration of 7 ms, an amplitude of 3-5 mA, and a frequency of 30 Hz. Blood glucose levels were measured in all of the rats every 2.5 minutes during from about 60 minutes until about 120 minutes, and at greater intervals thereafter.

As can be seen in the graph, glucose levels during the initial 60-minute fasting period were stable in both the control and stimulation rats. Blood glucose levels began to increase sharply in the control rats upon injection of the glucose solution into the stomach. The blood glucose levels peaked after about 50 minutes after the injection, and decreased slowly thereafter toward the control level. In the stimulated rats, upon injection blood glucose levels increased more slowly, and reached a lower peak, compared to the control rats. The area under the curves (i.e., the area between each of the curves and the normalized baseline determined during the 60-minute fasting period), which is related to total absorption of glucose, was about 66% lower in the stimulated rats than in the control rats. The inventors hypothesize that this electrical-stimulation-induced decrease in glucose absorption was caused by both delayed gastric emptying and increased intestinal flow, as demonstrated hereinabove with reference to FIGS. 8-12. Alternatively or additionally, the electrical stimulation induces the reduced glucose absorption via another pathway.

The majority of cases of type II diabetes are associated with the failure of beta cells to augment insulin secretion in response to an increasing demand for insulin from peripheral tissue. It is known that diminished first-phase insulin secretion is an early marker of beta-cell dysfunction, appearing before significant changes in absolute glucose concentrations are apparent. Studies of human subjects with impaired glucose tolerance (IGT) demonstrate multiple abnormalities in both qualitative and quantitative measures of insulin secretion. Among these abnormalities, first-phase insulin secretion is markedly reduced. Because of this reduced first-phase secretion, type II diabetics often do not experience the rapid increase in blood insulin level necessary for helping blood glucose enter peripheral cells.

In an embodiment of the present invention, intestinal electrical stimulation is applied, such as using the stimulation techniques described herein, to induce delayed gastric emptying. The resulting delay in and/or moderation of the rise of blood glucose concentration, as described hereinabove with reference to FIG. 13, enables the second-phase of insulin secretion to achieve blood glucose homeostasis, even in the absence of the first-phase insulin secretion. As a result, the large postprandial blood glucose fluctuations often experienced by diabetic patients are reduced. For some applications, such stimulation is applied upon detection of eating by the subject, or after a delay after the detection of eating.

In an embodiment of the present invention, an endoscopic surgical method is provided in which one or more electrodes are passed from the gastrointestinal tract and coupled to the vagus nerve. Typically, but not necessarily, the one or more electrodes are assembled generally as a nerve cuff (e.g., as is known in the art). During the endoscopic procedure, the electrodes are typically passed through an incision in the stomach and placed around a portion of the vagus nerve that innervates pancreas 30, such as the posterior vagal trunk. As appropriate, techniques described in the above-cited article by Kalloo et al. may be adapted to facilitate coupling of the electrodes to the vagus nerve.

For some applications, control unit 20 remains in the stomach, and is wirelessly coupled to the electrodes on the Vagus nerve or is coupled via wires passed through the wall of the gastrointestinal tract. Alternatively, the control unit is also passed through the incision in the stomach and implanted in the peritoneum. The control unit typically drives the electrodes to induce action potentials to propagate towards the pancreas in order to modulate insulin production. Alternatively or additionally, the control unit drives the electrodes to induce action potentials to propagate towards the brain, in order to simulate a natural pancreas-generated signal indicative of elevated blood glucose levels and to thereby cause the brain to invoke natural blood glucose level reduction mechanisms. In either case, the control unit typically drives the electrodes in response to a signal indicative of eating and/or indicative of an elevated blood glucose level. Action potentials propagating towards or away from the pancreas are typically induced by a current or field that is applied at between about 3 and about 50 Hz, e.g., between about 3 and about 20 Hz, or between about 10 and about 20 Hz. Alternatively or additionally, techniques and/or signal parameters described in (a) U.S. Pat. No. 5,188,104 to Wernicke et al., (b) U.S. Pat. No. 6,684,105 to Cohen et al., or (c) PCT Patent Publication WO 03/018118 to Cohen et al. or U.S. patent application Ser. No. 10/488,334 (granted as U.S. Pat. No. 7,734,355 to Cohen) in the national phase thereof, which are all incorporated herein by reference, are used or adapted for use in carrying out these applications of the present invention.

Figure 14:
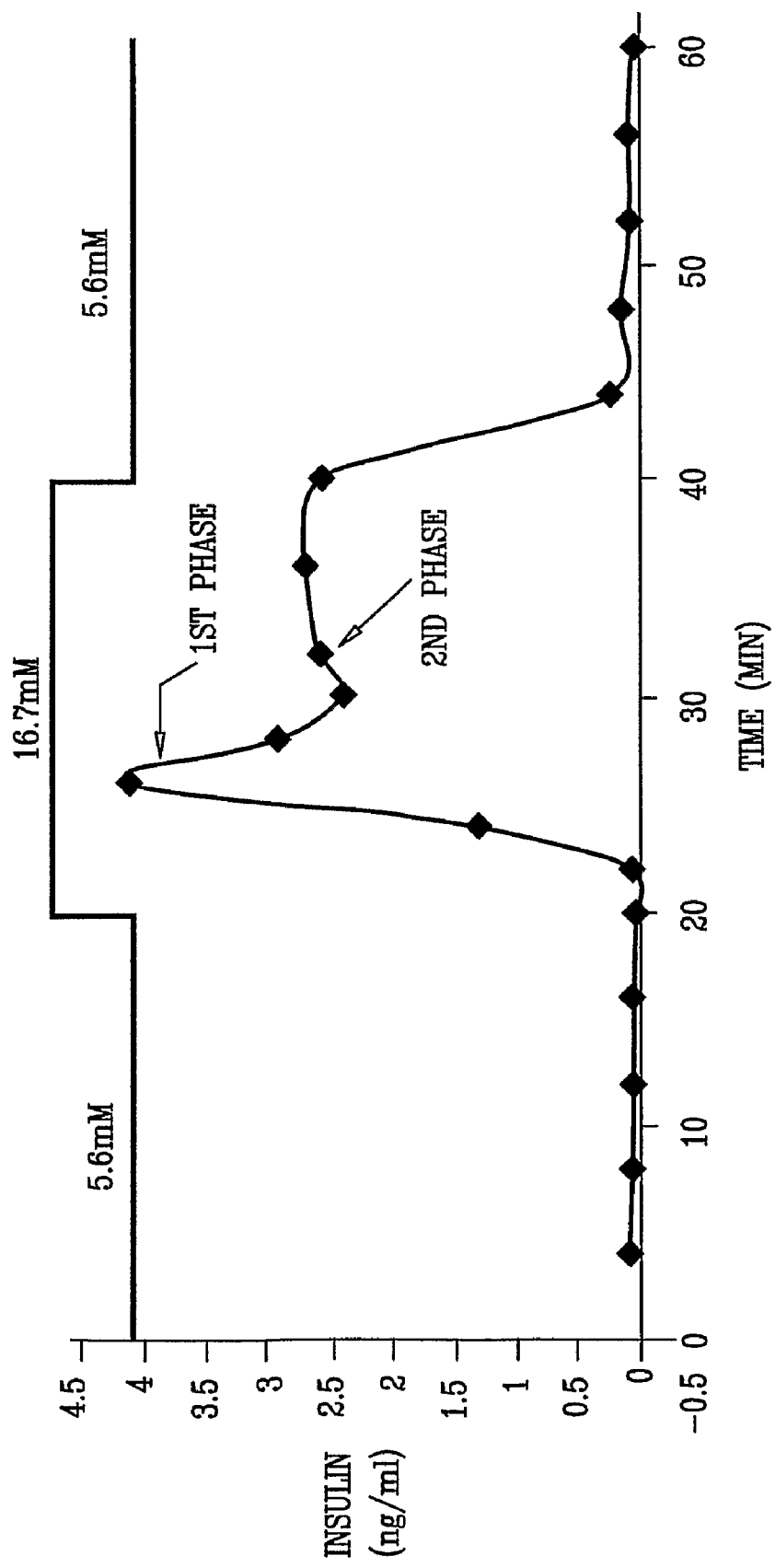
FIGS. 14-17 are graphs showing experimental results obtained during experiments performed in accordance with respective embodiments of the present invention.

FIG. 14 is a graph showing experimental results obtained during an experiment performed on a rat, in accordance with an embodiment of the present invention. The rat's in situ pancreas was perfused with a glucose solution of controlled concentration. Blood insulin levels were measured every few minutes based on samples drawn from the portal vein. Two wire ring electrodes were placed around the duodenum, at positions roughly corresponding the positions of electrodes 124 and 130 in FIG. 7. In the experiment shown in FIG. 14, no signal was applied to the duodenum through the electrodes. The concentration of glucose in the perfusion solution was varied from 5.6 mM in a first period, to 16.7 mM in a second period, and back to 5.6 mM in a third period. Each period lasted 20 minutes. Blood insulin levels during the first and third periods remained non-elevated, and rose to show a characteristic first and second phase insulin response during the second period.

Figure 15:
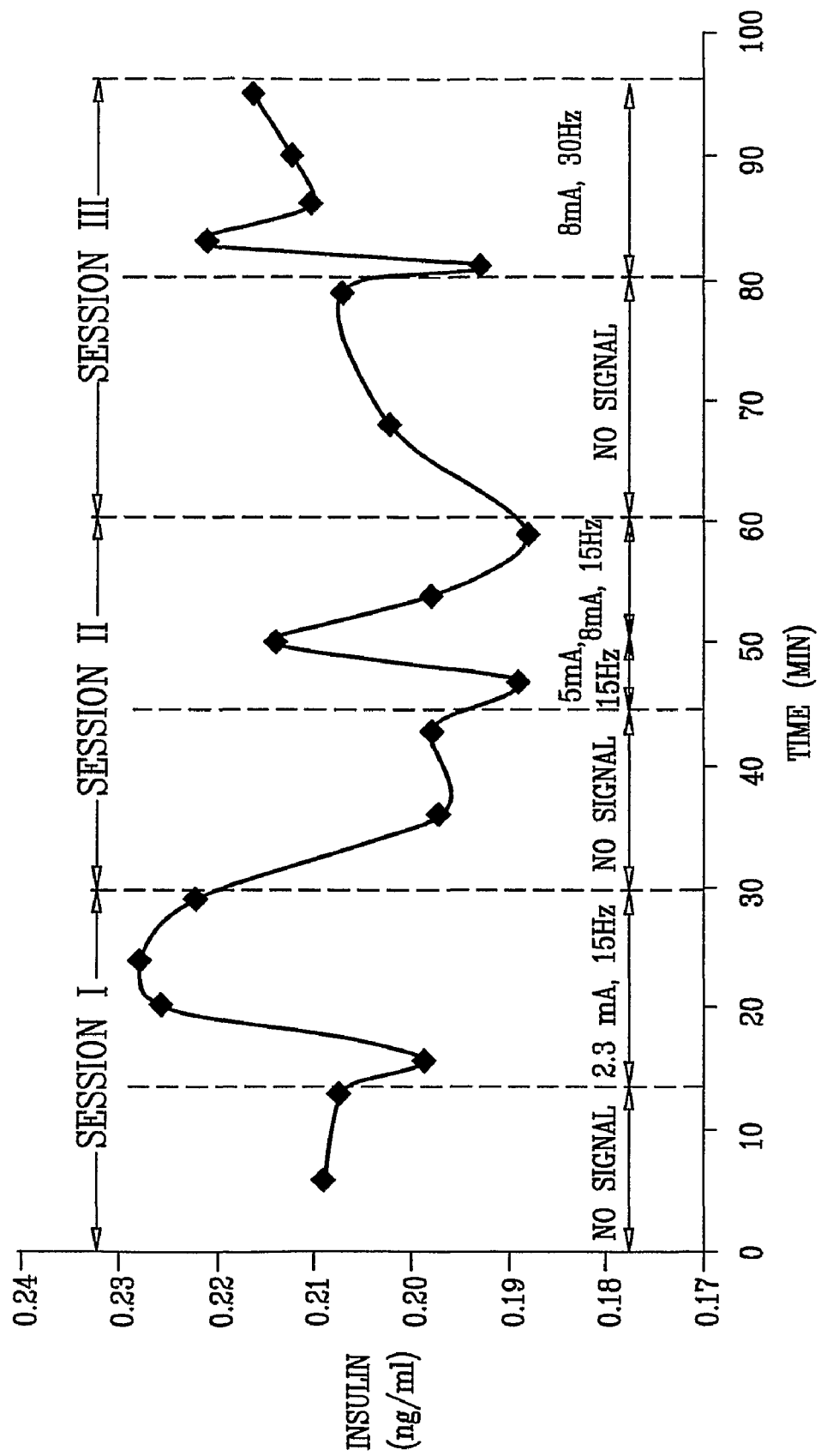

FIG. 15 is a graph showing experimental results obtained during an experiment performed on a different rat, in accordance with an embodiment of the present invention. In each of three consecutive sessions, each lasting approximately 15 minutes, a no-signal period was followed by a signal-application period. Peak insulin levels during each signal-application period are seen to be higher than the highest insulin level measured in any of the no-signal periods. The signals applied during the three sessions were as follows:
Session 1—2.3 mA, 15 Hz;
Session 2—5 mA, 15 Hz, followed after about 5 minutes by 8 mA, 15 Hz; and
Session 3—8 mA, 30 Hz.

Figure 16:
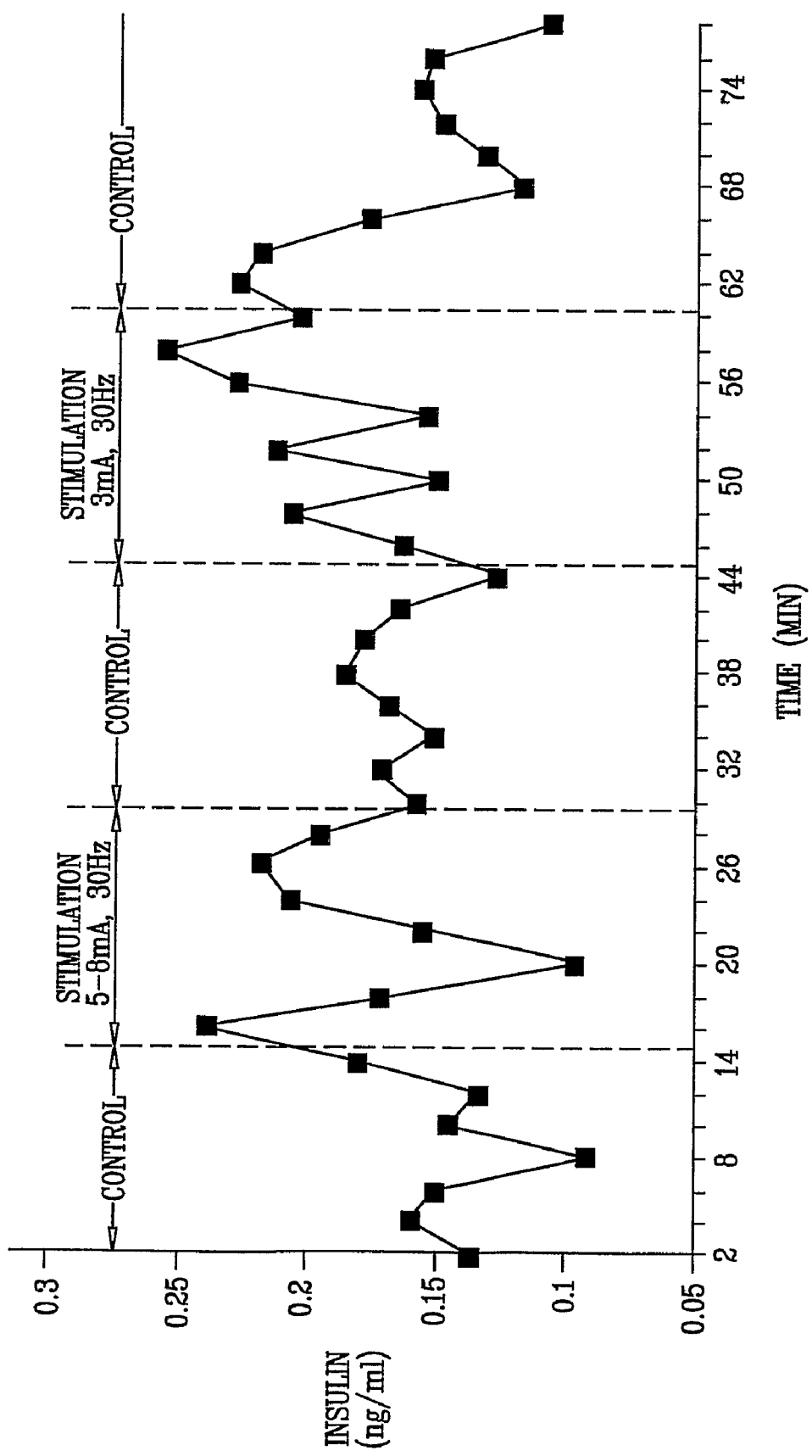

FIG. 16 is a graph showing experimental results obtained during an experiment performed on yet a different rat, in accordance with an embodiment of the present invention. During an experiment lasting about 1.3 h, two control (no-signal) periods were followed by signal-application periods in which the insulin levels rose significantly. A final control period after the second signal-application period showed a decrease in insulin level compared to the insulin level in the second signal-application period. The signal parameters during the two signal-application periods were (i) 5-8 mA, 30 Hz, and (ii) 3 mA, 30 Hz, respectively.

In each of these experiments, the signal was applied in repeated cycles of (a) signal application for one second, and (b) signal withholding for 44 seconds.

Figure 17:
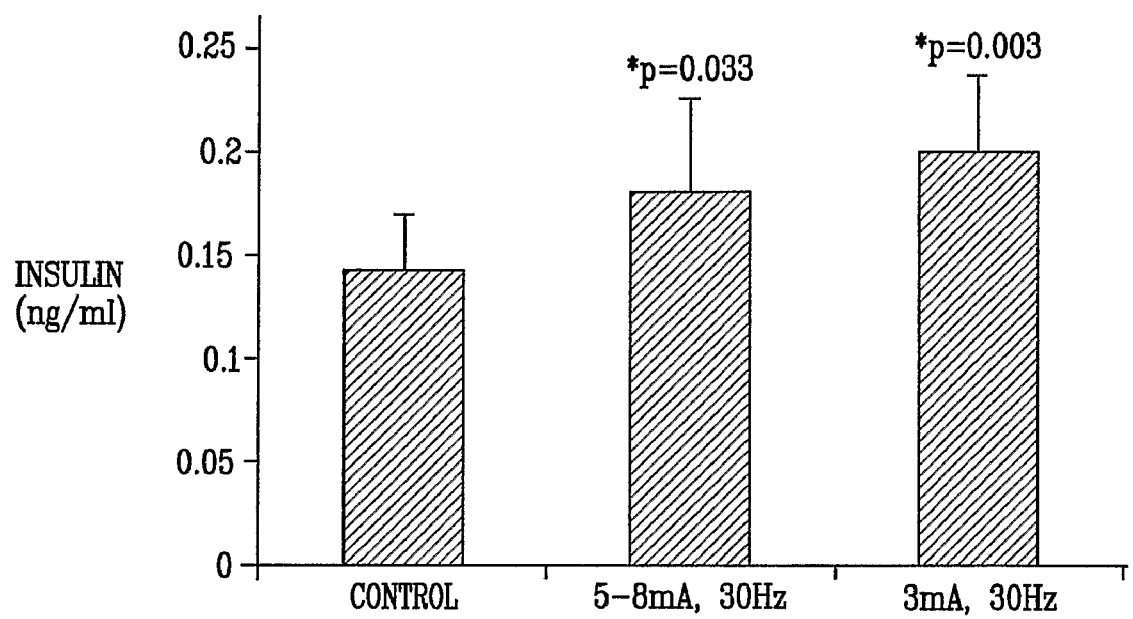

FIG. 17 is a bar chart, showing an analysis of the data shown in the graph of FIG. 16, in accordance with an embodiment of the present invention. It is seen that the blood insulin levels during both signal-application periods were significantly higher than those during the control periods.

In an embodiment of the present invention, a method for implanting an electrode is provided in which a lead comprising two or more independently-addressable electrodes is laparoscopically or endoscopically inserted into the tissue of the duodenal wall, until both electrodes are in the tissue and a distal tip of the lead emerges from the tissue. Typically, but not necessarily, sutures at one or more sites on the lead maintain the lead in position in the tissue. Alternatively, a fibrosis-inducing portion of the lead causes fibrosis at the portion, whereby the lead is held in place. In an embodiment, the electrodes have a plurality of legs extending therefrom, which reside partly or entirely within the tissue of the duodenal wall, and maintain the position of the electrodes partly or entirely within the tissue of the wall. Leads extending from the electrodes may pass through the lumen of the duodenum or outside of the duodenum in order to reach control unit 20.

For some applications, in addition to or instead of electrical insulin modulation techniques described herein, an implanted pump or external injections of insulin or another hormone or enzyme are utilized in order to control blood glucose levels or levels of one or more other blood components.

It is noted that embodiments of the present invention are generally described herein with respect to treatment of obesity and/or diabetes. The inventors hypothesize that embodiments of the present invention that treat a patient's obesity also treat diabetes, directly or indirectly. The inventors also hypothesize that embodiments of the present invention that treat a patient's diabetes also treat obesity, directly or indirectly. The scope of the present invention includes practice of the techniques described herein for treatment of other diseases, as well.

Some embodiments of the present invention are described herein with respect to driving a current into tissue. The scope of the present invention includes generating an electric field that affects the tissue in a corresponding fashion. For example, instead of driving currents having amplitudes in the range of milliamps, an electric field of 100's or 1000's of volts may be generated, typically having a similar or identical time profile as that of the described current. In an embodiment, such a field is generated by electrodes embedded in a sleeve such as is described in the above-cited Levine publication, and the electrodes are not necessarily in electrical contact with tissue which they affect.

It is noted that some embodiments of the present invention are described with respect to electrodes coupled by leads to a control unit. The scope of the present invention includes wireless coupling of the electrodes to the control unit, as well.

It is noted that some embodiments of the present invention are described with respect to electrodes in contact with or adjacent to muscle tissue. The scope of the present invention includes treating a condition such as obesity or diabetes via direct muscle stimulation by the electrodes, and/or via direct or indirect stimulation of a nerve fiber that innervates the muscle tissue (e.g., an enteric nervous system nerve fiber) or is close enough to the electrodes to be affected by the field generated by the electrodes. Alternatively or additionally, the same electrode may be driven simultaneously or at different times in accordance with muscle-stimulating and nerve-stimulating protocols.

It is noted that various techniques are described hereinabove for detecting eating or various stages of digestion (e.g., pyloric valve activity, peristalsis, segmentation). As appropriate, various sensors including electromyographic sensors, acceleration sensors, ultrasound sensors, or other sensors known in the art may be used for this purpose, and these may be located in or adjacent to the esophagus, stomach, cardiac or pyloric valves, or duodenum. Thus, for example, an ultrasound sensor may be placed adjacent to the duodenum in order to determine when the duodenum is full. In response to such a determination, one or more of the obesity or diabetes treatments described hereinabove may be performed.

In an embodiment, treatment apparatus comprises a capsule and a sensor. The sensor is adapted to sense when the capsule is near the sensor. The sensor is implanted adjacent to a gastrointestinal tract site of a patient. The patient swallows the capsule prior to or during a meal, and passage of the capsule within a small distance of the sensor is detected by the sensor and is used to trigger initiation of an obesity or diabetes treatment protocol. For some applications, the treatment protocol is carried out using apparatus described herein. In an embodiment, the capsule comprises a magnet, and the sensor comprises a magnetic switch that is opened or closed due to proximity of the magnet. Alternatively, the capsule comprises a coil or another passive element, and the sensor detects the proximity of the coil or other passive element using techniques known in the art. Further alternatively, the capsule comprises an active element, which transmits a low-power signal that is detected by the sensor.

For applications in which the sensor is coupled to the proximal duodenum, the capsule is typically less than one or two millimeters in diameter, so as to facilitate its expulsion through the pylorus at an early stage during digestion. To ease its handling by the patient, the capsule may be surrounded by a rapidly-dissolving outer coating, whose total diameter is similar to that of a standard pharmaceutical pill. For applications in which the sensor is coupled to the stomach, the capsule may be larger than two millimeters in diameter.

In an embodiment of the present invention, the systems described herein comprise an implanted or external blood glucose sensor, and stimulation is applied or modulated responsively to a sensed level of blood glucose. For some applications, stimulation is applied only when the blood glucose level exceeds a certain threshold, such as a level considered higher than a normal glucose level. Alternatively, a strength of the stimulation is increased as the blood glucose level increases. In this embodiment, the systems utilize a closed feedback loop.

In an embodiment of the present invention, the techniques described herein are used for regulating blood cholesterol levels, typically decreasing LDL and/or increasing HDL. For some applications, a method for regulating a level of at least one blood cholesterol constituent comprises identifying that a subject suffers from dyslipidemia, and using one or more of the techniques described herein to regulate the level responsively to the identifying.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising:
one or more electrodes, adapted to be placed in contact with a wall of a duodenum of a subject; and
a control unit, adapted to:
drive the electrodes to apply a current to the wall of the duodenum,
configure the current to stimulate a site selected from the group consisting of: a vagus nerve of the subject, and enteric nervous system (ENS) tissue of the subject,
configure the current in accordance with a set of parameters for the current, the set of parameters including a pulse width of pulses of the current and a frequency of application of the pulses, and
select the set of parameters to be such as to lower a level of glucose in blood of the subject and to be sufficient to cause closure of a pylorus of the subject.

2. The apparatus according to claim 1, wherein the site includes the vagus nerve of the subject, and wherein the control unit is adapted to configure the current to stimulate the vagus nerve.

3. The apparatus according to claim 1, wherein the site includes the ENS tissue of the subject, and wherein the control unit is adapted to configure the current to stimulate the ENS tissue.

4. The apparatus according to claim 1, comprising an eating sensor, and wherein the control unit is adapted to drive the electrodes to apply the current responsively to a signal from the eating sensor indicative of eating by the subject.

5. The apparatus according to claim 1, wherein the control unit is adapted to select the set of parameters to be such as to increase a level of insulin in blood of the subject.

6. The apparatus according to claim 1, wherein two of the one or more electrodes are adapted such that the two of the one or more electrodes, when in contact with the wall, are mutually spaced by a distance that is greater than the spacing between any other two of the one or more electrodes, when in contact with the wall, and wherein the distance is less than 3 cm.

7. The apparatus according to claim 1, wherein the control unit is adapted to (a) configure the current to include a plurality of pulses, and (b) set a frequency of application of the pulses to be at least 0.1 Hz.

8. The apparatus according to claim 7, wherein the control unit is adapted to set the frequency to be at least 1 Hz.

9. The apparatus according to claim 8, wherein the control unit is adapted to set the frequency to be at least 3 Hz.

10. The apparatus according to claim 1, wherein the control unit is adapted to configure the current to include a plurality of pulses, and wherein at least two consecutive ones of the pulses each have respective pulse widths that are less than 75 ms.

11. The apparatus according to claim 10, wherein the control unit is adapted to configure the pulse widths to be less than 30 ms.

12. The apparatus according to claim 11, wherein the control unit is adapted to configure the pulse widths to be less than 15 ms.

13. The apparatus according to claim 1, wherein the control unit is adapted to (a) configure the current to include a plurality of pulses, (b) set a frequency of application of the pulses to a desired frequency value, and (c) set pulse widths of at least two consecutive pulses to be less than a threshold pulse width, wherein a ratio of the threshold pulse width to the desired frequency value is less than 1000 ms/Hz.

14. The apparatus according to claim 13, wherein the ratio is less than 100 ms/Hz.

15. The apparatus according to claim 14, wherein the ratio is less than 10 ms/Hz.

16. The apparatus according to claim 1, wherein the control unit is adapted to configure the current to be sufficient to cause the closure of the pylorus via a nerve-mediated pathway, but to be insufficient to cause the closure of the pylorus via direct electrical stimulation of muscle tissue of the pylorus.

17. The apparatus according to claim 1, wherein the one or more electrodes comprise at least two electrodes adapted to be placed 2-5 cm from the pylorus.

18. The apparatus according to claim 1, wherein the one or more electrodes comprise at least two electrodes adapted to be placed 1-2 cm from the pylorus.

19. The apparatus according to claim 1, wherein all of the one or more electrodes are adapted to be placed 2-5 cm from the pylorus.

20. The apparatus according to claim 1, wherein all of the one or more electrodes are adapted to be placed 1-2 cm from the pylorus.

21. The apparatus according to claim 1, wherein the control unit is adapted to be placed in a gastrointestinal tract of the subject.

22. The apparatus according to claim 21, wherein the control unit is adapted to be placed in a stomach of the subject.

23. The apparatus according to claim 21, wherein the control unit is adapted to be implanted in the subject outside of the stomach, and to be wirelessly coupled to the electrodes.

24. The apparatus according to claim 21, wherein the control unit is adapted to be implanted in the subject outside of the stomach, and wherein the apparatus comprises wires configured to couple the control unit to the electrodes.

25. The apparatus according to claim 21, wherein the control unit is adapted to be placed outside of a body of the subject, and to be wirelessly coupled to the electrodes.

26. A method comprising:
applying a current to a wall of a duodenum of a subject;
configuring the current to stimulate a site selected from the group consisting of: a vagus nerve of the subject, and enteric nervous system (ENS) tissue of the subject, in accordance with a set of parameters for the current, the set of parameters including a pulse width of pulses of the current and a frequency of application of the pulses; and
selecting the set of parameters to be such as to lower a level of glucose in blood of the subject and to be sufficient to cause closure of a pylorus of the subject.

27. The method according to claim 26, wherein the site includes the vagus nerve of the subject, and wherein configuring comprises configuring the current to stimulate the vagus nerve.

28. The method according to claim 26, wherein the site includes the ENS tissue of the subject, and wherein configuring comprises configuring the current to stimulate the ENS tissue.

29. The method according to claim 26, comprising sensing eating by the subject, wherein applying the current comprises applying the current responsively to the sensed eating.

30. The method according to claim 26, wherein configuring the current comprises selecting the set of parameters to be such as to increase a level of insulin in blood of the subject.

31. The method according to claim 26, wherein applying the current comprises:
   placing a plurality of electrodes in contact with the wall of the duodenum such that two of the plurality of electrodes are mutually spaced by a distance that is greater than the spacing between any other two of the plurality of electrodes, when in contact with the wall, and wherein the distance is less than 3 cm; and
   driving the plurality of electrodes to apply the current.

32. The method according to claim 26, wherein configuring comprises configuring the current to include a plurality of pulses, and setting a frequency of application of the pulses to be at least 0.1 Hz.

33. The method according to claim 32, wherein setting the frequency comprises setting the frequency to be at least 1 Hz.

34. The method according to claim 33, wherein setting the frequency comprises setting the frequency to be at least 3 Hz.

35. The method according to claim 26, wherein configuring comprises configuring the current to include a plurality of pulses, and wherein at least two consecutive ones of the pulses each have respective pulse widths that are less than 75 ms.

36. The method according to claim 35, wherein configuring comprises configuring the pulse widths to be less than 30 ms.

37. The method according to claim 36, wherein configuring comprises configuring the pulse widths to be less than 15 ms.

38. The method according to claim 26, wherein configuring the current comprises (a) configuring the current to include a plurality of pulses, (b) setting a frequency of application of the pulses to a desired frequency value, and (c) setting pulse widths of at least two consecutive pulses to be less than a threshold pulse width, wherein a ratio of the threshold pulse width to the desired frequency value is less than 1000 ms/Hz.

39. The method according to claim 38, wherein the ratio is less than 100 ms/Hz.

40. The method according to claim 39, wherein the ratio is less than 10 ms/Hz.

41. The method according to claim 26, wherein configuring the current comprises configuring the current to be sufficient to cause the closure of the pylorus via a nerve-mediated pathway, but to be insufficient to cause the closure of the pylorus via direct electrical stimulation of muscle tissue of the pylorus.

42. The method according to claim 26, wherein applying the current comprises:
   placing a plurality of electrodes in contact with the wall of the duodenum, such that at least two of the plurality of electrodes are 2-5 cm from the pylorus; and
   driving the electrodes to apply the current.

43. The method according to claim 26, wherein applying the current comprises:
   placing a plurality of electrodes in contact with the wall of the duodenum, such that at least two of the plurality of electrodes are 1-2 cm from the pylorus; and
   driving the electrodes to apply the current.

44. The method according to claim 26, wherein applying the current comprises:
   placing one or more electrodes in contact with the wall of the duodenum such that all of the one or more electrodes are 2-5 cm from the pylorus; and
   driving the electrodes to apply the current.

45. The method according to claim 26, wherein applying the current comprises:
   placing one or more electrodes in contact with the wall of the duodenum such that all of the one or more electrodes are 1-2 cm from the pylorus; and
   driving the electrodes to apply the current.

* * * * *